US010478473B2

(12) United States Patent
Sen et al.

(10) Patent No.: US 10,478,473 B2
(45) Date of Patent: Nov. 19, 2019

(54) COMPOSITIONS AND METHODS OF USING ANTI-MULLERIAN HORMONE FOR TREATMENT OF INFERTILITY

(71) Applicants: University of Rochester, Rochester, NY (US); CENTER FOR HUMAN REPRODUCTION, New York, NY (US)

(72) Inventors: Aritro Sen, Rochester, NY (US); Norbert Gleicher, New York, NY (US); Vitaly A. Kushnir, Salt Lake City, UT (US)

(73) Assignees: THE CENTER FOR HUMAN REPRODUCTION (CHR), New York, NY (US); UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 15/554,238

(22) PCT Filed: Feb. 29, 2016

(86) PCT No.: PCT/US2016/020058
§ 371 (c)(1),
(2) Date: Aug. 29, 2017

(87) PCT Pub. No.: WO2016/140910
PCT Pub. Date: Sep. 9, 2016

(65) Prior Publication Data
US 2018/0236034 A1 Aug. 23, 2018

Related U.S. Application Data

(60) Provisional application No. 62/128,127, filed on Mar. 4, 2015.

(51) Int. Cl.
| | |
|---|---|
| *A61K 38/22* | (2006.01) |
| *A61K 38/24* | (2006.01) |
| *A61P 15/08* | (2006.01) |
| *A61K 45/06* | (2006.01) |
| *A61K 31/138* | (2006.01) |
| *A61K 31/7105* | (2006.01) |
| *C12N 15/113* | (2010.01) |

(52) U.S. Cl.
CPC ............ *A61K 38/22* (2013.01); *A61K 31/138* (2013.01); *A61K 31/7105* (2013.01); *A61K 38/24* (2013.01); *A61K 45/06* (2013.01); *A61P 15/08* (2018.01); *C12N 15/1136* (2013.01); *C12N 2310/11* (2013.01); *C12N 2310/12* (2013.01); *C12N 2310/14* (2013.01); *C12N 2310/141* (2013.01); *C12N 2310/16* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 5,484,768 A | 1/1996 | Donahue et al. | |
| 7,241,577 B2 * | 7/2007 | Seifer | A61K 38/22 435/7.1 |
| 2003/0124620 A1 * | 7/2003 | Seifer | A61K 38/22 435/7.2 |
| 2012/0046228 A1 | 2/2012 | Molina | |

FOREIGN PATENT DOCUMENTS

| | | | | |
|---|---|---|---|---|
| EP | 0271570 | * | 1/1988 | ............ A61K 37/02 |
| EP | 1074265 A1 | | 2/2001 | |
| WO | 8800054 A1 | | 1/1988 | |
| WO | 9200752 A1 | | 1/1992 | |
| WO | 03016514 A1 | | 2/2003 | |
| WO | WO03/016514 | * | 2/2003 | ............ C12N 5/06 |
| WO | 2009052119 A1 | | 4/2009 | |
| WO | 2011045202 A1 | | 4/2011 | |
| WO | WO 2013/190443 | * | 12/2013 | ............ A61K 38/22 |
| WO | WO 2014/164981 | * | 10/2014 | ............ A61K 38/22 |
| WO | 2015089321 A2 | | 6/2015 | |
| WO | 2016030901 A1 | | 3/2016 | |

OTHER PUBLICATIONS

Zhang et al., Reproducting Endocrinology, vol. 27, published Jan. 1, 2012, abstract P-503 (Year: 2012).*
Gorsic et al., J Clin Endocrinol Metab, Aug. 2017, 102(8):2862-2872 (Year: 2017).*
Bhattacharya et al., PLoS One 12(3): e0171355. https://doi.org/10.1371/journal.pone.0171355; 22 pages total (Year: 2017).*
Pirollo et al., Cancer Res. 2008; 68(5): 1247-1250 (Year: 2008).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Ragin R. C. et al., "Human Mullerian Inhibiting Substance: Enhanced Purification Imparts Biochemical Stability and Restores Antiproliferative Effects" 1992, Protein Expression and Purification, 3: 236-245.
La Marca A. et al., "Anti-Müllerian Hormone Measurement on any Day of the Menstrual Cycle Strongly Predicts Ovarian Response in Assisted Reproductive Technology" 2007, Human Reproduction, 22: 766-771.
Fong S. L. et al., "Anti-Mullerian Hormone as a Marker of Ovarian Function in Women after Chemotherapy and Radiotherapy for Haematological Malignancies" 2008, Human Reproduction, 23: 674-678.
Fallat M. E. et al., "Mullerian-Inhibiting Substance in Follicular Fluid and Serum: A Comparison of Patients with Tubal Factor Infertility, Polycystic Ovary Syndrome, and Endometriosis" 1997, Fertil Steril. 67: 962-965.

(Continued)

*Primary Examiner* — Christina M Borgeest
(74) *Attorney, Agent, or Firm* — Riverside Law LLP

(57) ABSTRACT

The present invention provides compositions and methods for the treatment of subjects with impaired fertility or at risk for impaired fertility. In certain aspects, the invention relates to increasing the level or activity of anti-Mullerian hormone (AMH) in a subject.

8 Claims, 23 Drawing Sheets

Specification includes a Sequence Listing.

(56) References Cited

OTHER PUBLICATIONS

Cook C. L. et al., "Relationship between Serum Mullerian-Inhibiting Substance and Other Reproductive Hormones in Untreated Women with Polycystic Ovary Syndrome and Normal Women" 2002, Fertil Steril. 77: 141-146.
Pigny P. et al., "Elevated Serum Level of Anti-Mullerian Hormone in Patients with Polycystic Ovary Syndrome: Relationship to the Ovarian Follicle Excess and to the Follicular Arrest" 2003, J. Clin. Endocrinol. Metab. 88: 5927-2962.
Visser J. A. et al., "Anti-Müllerian Hormone: An Ovarian Reserve Marker in Primary Ovarian Insufficiency" 2012, Nat. Rev. Endocrinol. 8: 331-341.
Osman P., "Rate and Course of Atresia during Follicular Development in the Adult Cyclic Rat" 1985, J. Reprod. Fertil. 73: 261-270.
Visser et al., "Increased Oocyte Degeneration and Follicular Atresia during the Estrous Cycle in Anti-Mullerian Hormone Null Mice" 2007, Endocrinology, 142: 4891-4899.
Durlinger A. L. L. et al., "Anti-Mullerian Hormone Inhibits Initiation of Primordial Follicle Growth in the Mouse Ovary" 2002, Endocrinology, 143: 1076-1084.
Durlinger A. L. L. et al., "Anti-Mullerian Hormone Attenuates the Effects of FSH on Follicle Development in the Mouse Ovary" 2001, Endocrinology, 142: 4891-4899.
Durlinger A. L. L. et al., "Control of Primordial Follicle Recruitment by Anti-Mullerian Hormone in the Mouse Ovary" 1999, Endocrinology, 140: 5789-5796.
Durlinger A. L. L. et al., "Regulation of ovarian function: the role of anti-Müllerian hormone" 2002, Reproduction, 124: 601-609.
Kim J. H. et al., "The Inhibitory Effects of Mullerian-Inhibiting Substance on Epidermal Growth Factor Induced Proliferation and Progesterone Production of Human Granulosa-Luteal Cells" 1992, J. Clin. Endocrinol. Metab., 75: 911-917.
Chang H.-M. et al., "Antimullerian Hormone Inhibits Follicle-Stimulating Hormone-Induced Adenylyl Cyclase Activation, Aromatase Expression, and Estradiol Production in Human Granulosa-Lutein Cells" 2013, Fertil. Steril. 100: 585-592.
di Clemente N. et al., "Inhibitory Effect of AMH upon the expression of aromatase and LH receptors by cultured granulosa cells of rat and porcine immature ovaries" 1994, Endocrine, 2: 553-558.
Visser J. A. et al., "Role of anti-Müllerian hormone and bone morphogenetic proteins in the regulation of FSH sensitivity" 2014, Mol. Cell. Endocrinol. 382: 460-465.
Pellatt L. et al., "Anti-Müllerian hormone reduces follicle sensitivity to follicle-stimulating hormone in human granulosa cells" 2011, Fertil. Steril., 96: 1246-1251.
Seifer D. B. et al., "Is AMH a regulator of follicular atresia?" 2014, J. Assist. Reprod. Genet., 31: 1403-1407.
Pierre A. et al., "Loss of LH-induced down-regulation of anti-Müllerian hormone receptor expression may contribute to anovulation in women with polycystic ovary syndrome" 2013, Hum. Reprod. 28: 762-769.
Prapa et al., "Effect of Anti-Müllerian hormone (AMH) and bone morphogenetic protein 15 (BMP-15) on steroidogenesis in primary-cultured human luteinizing granulosa cells through Smad5 signalling" 2015, J. Assist. Reprod. Genet., 32: 1079-1088.
Grossman et al., "Mullerian-inhibiting substance inhibits cytochrome P450 aromatase activity in human granulosa lutein cell culture" 2008, Fertil. Steril., 82: 1364-1370.
La Marca A. et al., "Anti-Mullerian hormone (AMH): what do we still need to know?" 2009, Hum. Reprod., 24: 2264-2275.
Parikh et al., "microRNA-181a has a critical role in ovarian cancer progression through the regulation of the epithelial-mesenchymal transition" 2014, Nat. Commun., 5: 2977.

Taylor et al., "TGF-β upregulates miR-181a expression to promote breast cancer metastasis" 2013, J. Clin. Invest., 123: 150-163.
Bhushan et al., "miR-181a promotes osteoblastic differentiation through repression of TGF-β signaling molecules" 2013, Int. J. Biochem. Cell. Biol., 45: 696-705.
Wang et al., "Critical role for transcriptional repressor Snail2 in transformation by oncogenic RAS in colorectal carcinoma cells" 2010, Oncogene, 29: 1787-1197.
Zhang et al., "MicroRNA-181a Suppresses Mouse Granulosa Cell Proliferation by Targeting Activin Receptor IIA" 2013, PLoS One 8: e59667.
Cossigny et al., "The effects of FSH and activin A on follicle development in vitro" 2012, Reproduction, 143: 221-229.
Yang et al., "miR-181b promotes cell proliferation and reduces apoptosis by repressing the expression of adenylyl cyclase 9 (AC9) in cervical cancer cells" 2014, FEBS Lett., 588: 124-130.
Zhuang et al., "MicroRNA-181a-mediated downregulation of AC9 protein decreases intracellular cAMP level and inhibits ATRA-induced APL cell differentiation" 2014, Cell. Death Dis., 5: e1161.
Nomura et al., "Activin stimulates CYP19A gene expression in human ovarian granulosa cell-like KGN cells via the Smad2 signaling pathway" 2013, Biochem. Biophys. Res. Commun., 436: 443-448.
Sen A. et al., "Granulosa cell-specific androgen receptors are critical regulators of ovarian development and function" 2010, Mol. Endocrinol., 24: 1393-1403.
Sen A. et al., "Androgens regulate ovarian follicular development by increasing follicle stimulating hormone receptor and microRNA-125b expression" 2014, Proc. Natl. Acad. Sci. USA, 111: 3008-3013.
Kelsey T. M. et al., "A Validated Model of Serum Anti-Müllerian Hormone from Conception to Menopause" 2011, PLoS One, 6: e22024.
Griesinger G. et al., "Elimination Half-Life of Anti-Müllerian Hormone" 2012, The Journal of Clinical Endocrinology and Metabolism, 97: 2160-2163.
Tal et al., "Characterization of women with elevated antimüllerian hormone levels (AMH): correlation of AMH with polycystic ovarian syndrome phenotypes and assisted reproductive technology outcomes" 2014, American Journal of Obstetrics and Gynecology, 211: e51-58.
Gleicher N. et al., "Anti-Mullerian hormone (AMH) defines, independent of age, low versus good live-birth chances in women with severely diminished ovarian reserve" 2010, Fertility and Sterility, 94: 2824-2827.
McGee E. A. et al., "Initial and Cyclic Recruitment of Ovarian Follicles" 2000, Endocrine Reviews, 21: 200-214.
Kalich-Philosoph et al., "Cyclophosphamide Triggers Follicle Activation and "Burnout"; AS101 Prevents Follicle Loss and Preserves Fertility" 2013, Science Translational Medicine, 5: 185ra62.
Ma X. et al., "Leptin-Induced CART (Cocaine- and Amphetamine-Regulated Transcript) Is a Novel Intraovarian Mediator of Obesity-Related Infertility in Females" 2016, Endocrinology, 157: 1248-1257.
Sen A. et al., "Paxillin mediates extranuclear and intranuclear signaling in prostate cancer proliferation" 2012, J. Clin. Invest., 122: 2469-2481.
Evaul K. et al., "Cross-talk between G Protein-coupled and Epidermal Growth Factor Receptors Regulates Gonadotropin-mediated Steroidogenesis in Leydig Cells" 2008, J. Biol. Chem., 283: 27525-27533.
Bedecarrats et al., "Regulation of gonadotropin gene expression by Müllerian inhibiting substance" 2003, PNAS, 100: 9348-9353.
Prizant H. et al., "Androgen actions in the ovary: balance is key" 2014, J. Endocrinol., 222: R141-151.

* cited by examiner

COMPOSITIONS AND METHODS OF USING ANTI-MULLERIAN HORMONE FOR TREATMENT OF INFERTILITY

CROSS-REFERENCE TO RELATED APPLICATIONS

This application is a U.S. national phase application filed under 35 U.S.C. § 371 claiming benefit to International Patent Application No. PCT/US2016/020058, filed Feb. 29, 2016, which claims priority under 35 U.S.C. § 119(e) to U.S. Provisional Patent Application No. 62/128,127 filed Mar. 4, 2015, the contents of which are incorporated by reference herein in their entirety.

BACKGROUND OF THE INVENTION

Ovarian follicles are the basic units of female reproductive biology that contain a single oocyte (immature ovum or egg). These structures are periodically initiated to grow and develop, culminating in ovulation of usually a single oocyte in humans. These eggs/ova are developed only once every menstrual cycle (e.g. once a month in humans). A woman begins menstrual cycle at puberty with about 400,000 follicles. These dormant follicles are called primordial follicles. Once these follicles start growing they pass through different stages of follicular development; primary follicles, pre-antral follicles, antral and preovulatory follicles.

Anti-Müllerian hormone (AMH), also known as Müllerian inhibiting substance (MIS) or factor (MIF), has well defined roles in male sex differentiation. Across the female reproductive lifespan the role of AMH has, however, only more recently come to light. AMH is produced by granulosa cells (GCs) in small, growing ovarian follicles, and plays an important role in folliculogenesis. AMH acts as a natural follicular gatekeeper limiting follicle growth initiation and maintains the primordial follicle pool throughout the reproductive age. AMH is considered an intra-ovarian regulator that inhibits follicular atresia (death) at later stages of follicle development. Thus, if there is less AMH, then the initiation of primordial follicle growth becomes unchecked and follicles are lost faster than normal, resulting in a pathophysiological condition called diminished ovarian reserve (DOR) also known as premature ovarian aging (POA) and in some cases primary ovarian insufficiency (POI). Another common pathophysiological condition in women called polycystic ovary syndrome (PCOS) characterized by excessive follicle recruitment and arrest in the antral stage, resulting in impaired ovulation. These small follicles in PCOS produce high levels of AMH. AMH correlates to functional ovarian reserve, and is, therefore, used as a diagnostic and prognostic marker in infertility and in reproductive disorders like polycystic ovary syndrome (PCOS) (Fallet et al., 1997, Fertil Steril 67:962-5; Cook et al., 202, Fertil Steril 77:141-6; Pigny et al., 2003, J Clin Endocrinol Metab 88:5957-62) and POI (Visser et al., 2012, Nat Rev Endocrinol 8:331-41). It is also now routinely used to predict a ovarian response in in vitro fertilization (IVF) and other types of fertility treatment. Understanding AMH actions may, therefore, provide insights into follicular development under normal as well as pathophysiological conditions.

During folliculogenesis, AMH is expressed in GCs immediately following recruitment of follicles from the dormant primordial pool into the growing follicle pool, and continues to increase until follicles reach preantral and antral stages. Thereafter, AMH expression decreases and becomes undetectable during cyclic selection (Visser et al., 2012, Nat Rev Endocrinol 8:331-41). AMH expression is also absent in atretic follicles (Osman, 1985, J Reprod Fertil 73:261-70) and, notably, is considered an intra-ovarian inhibitor of follicular atresia (Visser et al., 2007, Endocrinology 148:2301-8).

AMH knockout (AMHKO) mouse model (Durlinger et al., 2002, Endocrinology 143:1076-84; Durlinger et al., 2001, Endocrinology 142:4891-9; Durlinger et al., 1999, 140:5789-96; Durlinger et al., 2002, Reproduction 124:601-9) provide major insights into AMH actions in folliculogenesis. AMH-deficient mice have significantly more growing follicles and develop POI. The AMH null mice demonstrated that ovarian AMH directly or indirectly prevents or inhibits primordial follicles from entering the pool of growing follicles. Interestingly, several previous in vitro studies in GCs (Durlinger et al., 2001, Endocrinology 142:4891-9; Durlinger et al., 2002, Reproduction 124:601-9; Kim et al., 1992, J Clin Endocrinol Metab 75:911-7; Chang et al., 2013, Fertil Steril 100:585-92 e581) have shown inhibitory effects of AMH on FSH-induced processes like proliferation, aromatase activity and luteinizing hormone receptor (LHR) expression across species (Clemente et al., 1994, Endocrine 2:553-8). Additionally, using an in vitro mouse follicle culture system, it also been reported that AMH inhibits FSH-stimulated follicle growth by decreasing the sensitivity of ovarian follicles to FSH (Durlinger et al., 2001, Endocrinology 142:4891-9; Visser and Themmen, 2014, Mol Cell Endocrinol 382:460-5). These in vivo and in vitro studies have established that, in addition to inhibiting the outgrowth of primordial follicles, AMH also inhibits FSH-stimulated follicle growth. Despite these studies and the wide utilization of AMH as a diagnostic and prognostic clinical marker, underlying mechanisms of AMH that regulate FSH actions and folliculogenesis, are still only poorly understood.

Thus, while the physiological regulatory role of AMH may be understood, there still a need in the art for compositions and methods utilizing AMH for treatment of women with impaired follicular development. The present invention satisfies this unmet need.

SUMMARY OF THE INVENTION

In one aspect, the present invention provides a method for treating infertility in a subject. The method comprises administering to the subject an effective amount of anti-Mullerian hormone (AMH) at a dose in the range of about 100 ng/day to about 44,000 ng/day for a period of time from about 30 days to about 90 days. In one embodiment, the method comprises administering AMH at a dose in the range of about 22,000 ng/day to about 44,000 ng/day.

In one embodiment, infertility in the subject is characterized by at least one selected from the group consisting of diminished ovarian reserve (DOR), natural aging, premature ovarian aging, and gonadotoxic treatment.

In one aspect, the invention provides a method of increasing the number of collected oocytes during superovulation in a subject. The method comprises administering to the subject an effective amount of AMH each day for a first period of time and inducing superovulation in the subject after a second period of time where no AMH is delivered to the subject.

In one embodiment, superovulation is induced by administering to the subject at least one selected from the group consisting of a gonadotropin, follicle stimulating hormone (FSH), luteinizing hormone (LH), clomiphene, a selective estrogen-receptor modulator (SERM), and a aromatase inhibitor.

In one embodiment, the first period of time is in the range of about 1 day to about 90 days. In one embodiment, AMH is administered at a dose in the range of about 22,000 ng/day to about 44,000 ng/day, for a first duration of about 90 days. In one embodiment, the second period of time is in the range of about 0 days to about 30 days.

In one embodiment, the present invention provides a formulation for treating infertility comprising anti-Mullerian hormone (AMH). In one embodiment, the formulation comprises a composition for stabilization, comprising a surfactant, a buffer, and a liquid medium, and has a pH from about 5 to about 8.

In another aspect, the present invention provides a method for modulating folliculogenesis in a subject in need thereof, the method comprising a modulator of anti-Mullerian hormone (AMH), miR-181a, miR-181b or any combination thereof.

In one embodiment, the modulator is an inhibitor of AMH, miR-181a, or miR-181b. In one embodiment, the inhibitor of miR-181a increases acvr2A expression. In another embodiment, the inhibitor of miR-181b increases ADCY9 expression.

In one embodiment, the inhibitor is selected from the group consisting of an siRNA, a ribozyme, an antisense, an aptamer, a peptidomimetic, an antibody, a peptide, a small molecule, and combinations thereof.

In one embodiment, the subject is human. In another embodiment, the subject has a disease selected from the group consisting of polycystic ovary syndrome (PCOS) and primary ovarian insufficiency (POI).

In some embodiments, the modulator is an activator of AMH, miR-181a, or miR-181b. In one embodiment, the activator of AMH is AMH. In another embodiment, the activator of miR-181a is miR-181a. In yet another embodiment, the activator of miR-181b is miR-181b.

The present invention also provides a composition for stimulating folliculogenesis, the composition comprising an inhibitor of a microRNA (miR), wherein the miR is selected from the group consisting of miR-181a, miR-181b and a combination thereof. In one embodiment, the composition further comprises a pharmaceutically acceptable carrier.

In one embodiment, the invention provides a formulation for treating infertility in a subject, where the formulation comprises miR-181a, miR-181b, or a combination thereof. In one embodiment, the formulation further comprises a composition for stabilization, wherein the composition for stabilization comprises a surfactant, a buffer, and a liquid medium, and has a pH from about 5 to about 8.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3, comprising

FIG. 4, comprising

FIG. 5, comprising

FIG. 6, comprising FIG. 6A: miR-181 levels in (1) mouse primary granulosa cell (GC) cultures isolated from 8-9 weeks old animals treated with 10 ng/ml of AMH for 18 h and (2) ovaries isolated from 8-9 weeks old mice treated daily for 4 weeks with 300 ng of AMH injections. FIG. 6B: Intracellular cAMP levels in primary granulosa cell (GC) cultures treated with/without 10 ng/ml of AMH in presence or absence of an anti-miR-181. Data is represented as ±SEM, n=3 and *P≤0.05

FIG. 7A and FIG. 7B, depicts the results of experiments where pre-pubertal and 8-9 week old mice were pre-treated with AMH (300 ng) or vehicle for 4 weeks followed by 12 days of no treatment and then subjected to superovulation regime. Oocyte/cumulus masses were surgically isolated from the oviduct and ampulla and counted as described previously (Sen et al., 2010, Mol Endocrinol, 24(7): 1393-403; Sen et al., 2014, Proc Natl Acad Sci USA, 111(8): 3008-13). Data is represented as ±SEM, n=3 and *P≤0.05

FIG. 8, comprising FIG. 8A depicts histological analysis of ovarian morphology of pre-pubertal mice. FIG. 8B depicts histological analysis of ovarian morphology of reproductive age 8-9 week old mice. Mice (n=5 ovaries from five different mice/age group) were subjected to daily IP injection of AMH (120 ng or 300 ng) or vehicle for 4 weeks. P-primordial; Pr-primary; PA-preantral; A-antral; Atr-atretic; CL-Corpus luteum. *P≤0.05 vs Control.

FIG. 9, comprising FIG. 9A depicts 8-9 week old animals were subjected to daily IP injection of vehicle (5 animals/treatment) for 4 weeks and estrous cycle was determined by daily vaginal smears. FIG. 9B depicts 8-9 week old animals were subjected to daily IP injection of 120 ng of AMH (5 animals/treatment) for 4 weeks and estrous cycle was determined by daily vaginal smears. FIG. 9C depicts 8-9 week old animals were subjected to daily IP injection of 300 ng of AMH (5 animals/treatment) for 4 weeks and estrous cycle was determined by daily vaginal smears. Individual lines in each plot represent estrous cycle of a single animal. P-proestrous; D-diestrous and E-estrus.

FIG. 10, comprising FIG. 10A depicts ovaries isolated following the treatment to determine relative mRNA levels of genes involved in folliculogenesis. FIG. 10B depicts blood collected by cardiac puncture following the treatment to determine serum estradiol levels. AR-androgen receptor; StAR-steroidogenic acute regulatory protein; FSHR-ollicle stimulating hormone; PR-progesterone receptor; LHR-luteinizing hormone receptor; ERα-estrogen receptor alpha. *P≤0.05 vs Control.

FIG. 11, comprising FIG. 11A depicts results from experiments where pre-antral follicles from ovaries of 21 d old female mice were mechanically isolated and cultured in vitro for 4 days in the presence of FSH (10 ng/ml) with/without AMH (5 and 10 ng/ml). Follicular growth was determined as a measure of increase in follicular diameter of individual follicles from the beginning to the end of culture. Data is represented as the average increase in diameter (10 follicles/treatment) isolated from 5 separate animals. FIG. 11B depicts experiments where primary cultures of mouse granulosa cells (GCs) were treated with FSH in presence or absence of different concentration of AMH for 18 h. Thereafter relative expression of aromatase mRNA was determined. FIG. 11C depicts experiments where primary cultures of mouse granulosa cells (GCs) were treated with FSH in presence or absence of different concentration of AMH for 18 h. Thereafter relative expression of intracellular cAMP was determined. *P≤0.05 vs Control.

FIG. 12, comprising FIG. 12A depicts Relative expression of miR-181a levels in primary mouse granulosa cells (GCs) treated with 10 ng/ml AMH and in ovaries isolated from 8-9 week old animals subjected to daily IP injection of 300 ng/ml AMH for 4 weeks. FIG. 12B depicts Relative expression of miR-181b levels in primary mouse granulosa cells (GCs) treated with 10 ng/ml AMH and in ovaries isolated from 8-9 week old animals subjected to daily IP injection of 300 ng/ml AMH for 4 weeks. *P≤0.05 vs 0 AMH.

FIG. 13, comprising FIG. 13A depicts relative levels of acvr2A mRNA. FIG. 13B depicts relative levels of acvr2A protein. *P≤0.05 vs NSP Control.

FIG. 14, comprising FIG. 14A depicts relative levels of ADCY9 mRNA. FIG. 14B depicts relative levels of ADCY9 protein. FIG. 14C depicts FSH-stimulated cAMP levels. *P≤0.05 vs NSP Control.

FIG. 15, comprising FIG. 15A depicts experiments where pre-pubertal mice were treated with AMH (300 ng) or vehicle for 4 weeks followed by 12 days of no treatment (n=5 animals/treatment). Thereafter these animals were subjected to superovulation regime (5U PMSG; 5U hCG) oocyte/cumulus masses were surgically isolated from the oviduct and counted. FIG. 15B depicts experiments where 8-9 week old mice were treated with AMH (300 ng) or vehicle for 4 weeks followed by 12 days of no treatment (n=5 animals/treatment). Thereafter these animals were subjected to superovulation regime (5U PMSG; 5U hCG) oocyte/cumulus masses were surgically isolated from the oviduct and counted. *P≤0.05 vs Control.

FIG. 17, comprising FIG. 17A depicts the relative expression of acvr2A. FIG. 17B depicts AC9 mRNA levels. FIG. 17C depicts intracellular cAMP levels.

DETAILED DESCRIPTION

Figure 1:
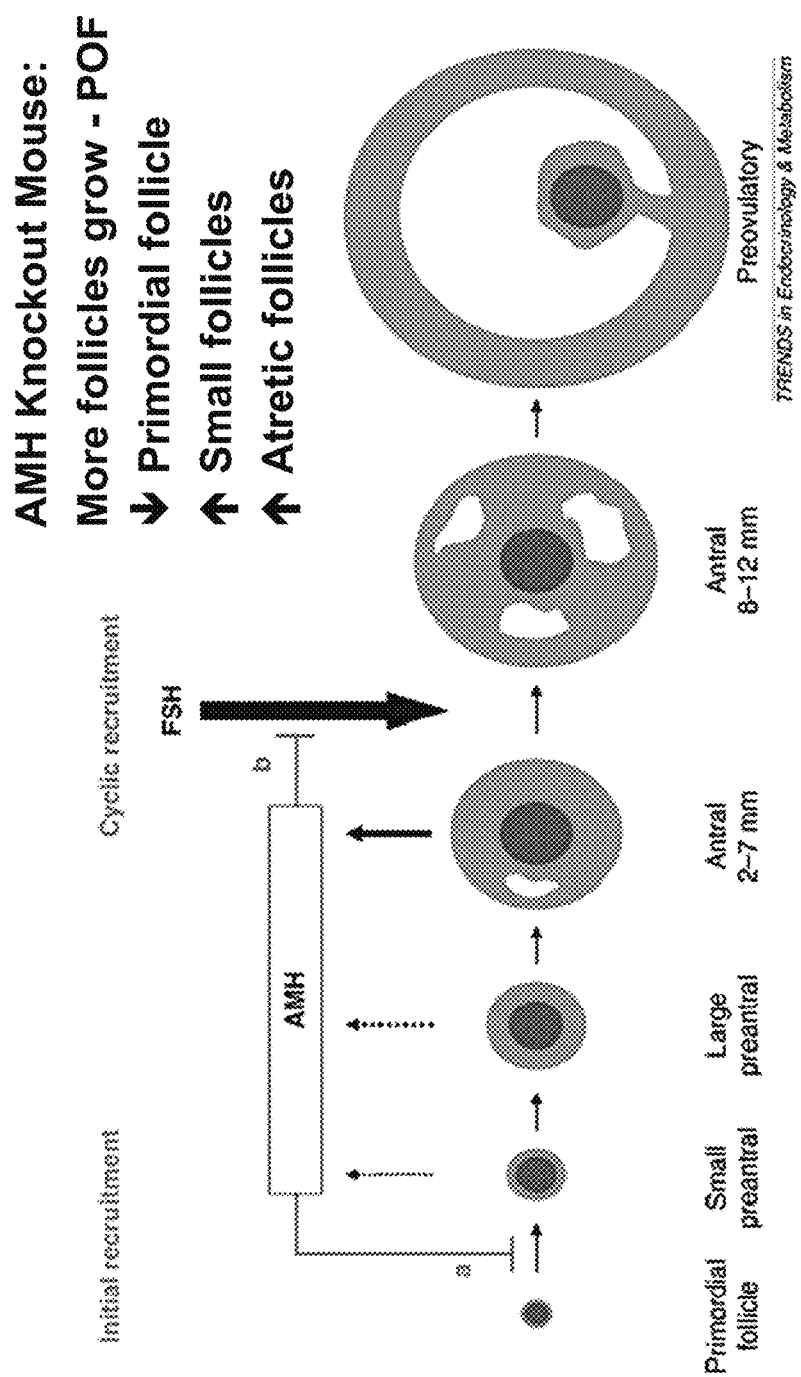
FIG. 1 is a schematic depicting the effect of AMH on follicular development.

The present invention relates to compositions and methods for treating a subject with impaired fertility or a subject at risk for impaired fertility. In certain embodiments, the invention relates to compositions and methods for increasing the level or activity of anti-Mullerian hormone (AMH) in a subject, which results in the accumulation of small follicles and prevents depletion of follicles. For example, in certain embodiments, the invention relates to the treatment of a subject with diminished ovarian reserve or premature ovarian aging, which is characterized by reduced number of follicles available for maturation and ovulation. In certain embodiments, the invention relates to the treatment of a subject who is undergoing, or will undergo, a gonadotoxic treatment, for example chemotherapy, which may induce rapid or complete follicle depletion.

In certain aspects, the present invention relates to compositions and methods for increasing the expression or activity of AMH, also known as Mullerian-inhibiting factor (MIF), Mullerian-inhibiting substance (MIS), and Mullerian-inhibiting hormone (MIH). The present invention is based in part on the discovery that administration of AMH results in the accumulation of small immature follicles, thereby preventing follicle maturation. Thus, in certain instances AMH can be used to conserve follicles until desired. Further, it is demonstrated herein that pre-treatment of AMH in subjects receiving controlled ovarian hyperstimulation (superovulation) increases the yield of oocytes, which can then be used for subsequent intrauterine insemination, in vitro fertilization (IVF), or cryopreservation.

In one embodiment, the invention provides a composition comprising AMH. In one embodiment, the composition comprises an amount of AMH that results in accumulation of immature follicles while not providing excessive AMH that may have negative implications on follicular development. For example, in one embodiment, the composition is configured for delivery of about 100 ng/day to about 44,000 ng/day AMH to the subject.

In one embodiment, the invention provides a method of treating a subject having impaired fertility or at risk for impaired fertility, comprising administering to the subject an effective amount of a composition which increases the expression or activity of AMH. For example, in one embodiment, the method comprises administering AMH to the subject. In one embodiment, AMH is administered to the subject at a dose of about 100 ng/day to about 44,000 ng/day.

In certain embodiments, the present invention relates to compositions and methods related to preventing follicle maturation by increasing the activity or expression of one or more downstream targets of AMH, including, but not limited to miR-181a, miR-181b, acvr2A, ADCY9, and cAMP. For example, it is demonstrated herein that AMH prevents maturation of follicles via upregulating the expression of miR-181a and miR-181b.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques, or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1988; Houston et al., 1988; Bird et al., 1988).

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

As used herein, a disease or disorder is "alleviated" if the severity of a symptom of the disease or disorder, the frequency with which such a symptom is experienced by a patient, or both, are reduced.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

As used herein, the terms "conservative variation" or "conservative substitution" as used herein refers to the replacement of an amino acid residue by another, biologically similar residue. Conservative variations or substitutions are not likely to substantially change the shape and/or activity of the peptide chain. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit, such as reducing, alleviating or preventing a symptoms associated with a condition.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Instructional material," as that term is used herein, includes a publication, a recording, a diagram, or any other medium of expression which can be used to communicate the usefulness of the nucleic acid, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

By describing two peptides or polypeptides as "operably fused" is meant that the structure and/or biological activity of each individual peptide is also present in the fusion.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, a "peptidomimetic" is a compound containing non-peptidic structural elements that is capable of mimicking the biological action of a parent peptide. A peptidomimetic may or may not comprise peptide bonds.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

A "prophylactic" treatment is a treatment administered to a subject who does not exhibit signs of a disease or exhibits only early signs of the disease for the purpose of decreasing the risk of developing pathology associated with the disease.

"Ribozymes" as used herein are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules. Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053).

The term "substantially pure" describes a compound, e.g., a protein or polypeptide, which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides, by column chromatography, gel electrophoresis or HPLC analysis. A compound, e.g., a protein, is also substantially purified when it is essentially free of naturally associated components or when it is separated from the native contaminants which accompany it in its natural state.

As used herein, the term "substantially the same" amino acid sequence is defined as a sequence with at least 70%, preferably at least about 80%, more preferably at least about 85%, more preferably at least about 90%, even more preferably at least about 95%, and most preferably at least 99% homology with another amino acid sequence, as determined by the FASTA search method in accordance with Pearson & Lipman, 1988, Proc. Natl. Inst. Acad. Sci. USA 85:2444-48.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound or composition that will elicit the biological or medical response of a tissue, system, or subject that is being sought by the researcher, veterinarian, medical doctor or other clinician. The term "therapeutically effective amount" includes that amount of a compound or composition that, when administered, is sufficient to prevent development of, or alleviate to some extent, one or more of the signs or symptoms of the disorder or disease being treated. The therapeutically effective amount will vary depending on the compound or composition, the disease and its severity and the age, weight, etc., of the subject to be treated.

To "treat" a disease as the term is used herein, means to reduce the frequency or severity of at least one sign or symptom of a disease or disorder experienced by a subject.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

The term "pharmaceutical formulation" refers to a preparation which is in such form as to permit the biological activity of the active ingredient to be effective, and which contains no additional components which are unacceptably toxic to a subject to which the formulation would be administered.

A "stable" or "stabilized" formulation is one in which the protein therein essentially retains its physical and/or chemical stability upon storage. Stability can be measured at a selected temperature for a selected time period. Preferably, the formulation is stable at room temperature (30° C.) or at 40° C. for at least 1 month and/or stable at about 2-8° C. for at least 1 year and preferably for at least 2 years. For example, the extent of aggregation during storage can be used as an indicator of protein stability. Thus, a "stable" formulation may be one wherein less than about 10% and preferably less than about 5% of the protein is present as an aggregate in the formulation. Various analytical techniques for measuring protein stability are available in the art and are reviewed, for example, in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993).

The term "aqueous solution" refers to a solution in which water is the dissolving medium or solvent. When a substance dissolves in a liquid, the mixture is termed a solution. The dissolved substance is the solute, and the liquid that does the dissolving (in this case water) is the solvent.

The term, "stabilizing agent" or "stabilizer" as used herein is a chemical or compound that is added to a solution or mixture or suspension or composition or therapeutic composition to maintain it in a stable or unchanging state; or is one which is used because it produces a reaction involving changes in atoms or molecules leading to a more stable or unchanging state.

A "reconstituted" formulation is one which has been prepared by dissolving a lyophilized protein or antibody formulation in a diluent such that the protein is dispersed in the reconstituted formulation. The reconstituted formulation is suitable for administration (e.g., parenteral administration) to a patient to be treated with the protein of interest and, in certain embodiments of the invention, may be one which is suitable for subcutaneous administration.

"Surfactants" are surface active agents that can exert their effect at surfaces of solid-solid, solid-liquid, liquid-liquid, and liquid-air because of their chemical composition, containing both hydrophilic and hydrophobic groups. These materials reduce the concentration of proteins in dilute solutions at the air-water and/or water-solid interfaces where proteins can be adsorbed and potentially aggregated. Surfactants can bind to hydrophobic interfaces in protein formulations. Proteins on the surface of water will aggregate, particularly when agitated, because of unfolding and subsequent aggregation of the protein monolayer.

"Surfactants" can denature proteins, but can also stabilize them against surface denaturation. Generally, ionic surfactants can denature proteins. However, nonionic surfactants usually do not denature proteins even at relatively high concentrations (1% w/v). Most parentally acceptable non-ionic surfactants come from either the polysorbate or polyether groups. Polysorbate 20 and 80 are contemporary surfactant stabilizers in marketed protein formulations. However, other surfactants used in protein formulations include Pluronic F-68 and members of the "Brij" class. Non-ionic surfactants can be sugar based. Sugar based surfactants can be alkyl glycosides. The general structure of the alkyl glycoside is $R_1$—O—$(CH_2)x$—R, where R is independently $CH_3$ or cyclohexyl ($C_6H_{11}$) and $R_1$ is independently glucose or maltose. Exemplary alkyl glycosides include those in which $R_1$ is glucose, R is $CH_3$, and x is 5 (n-hexyl-β-D-glucopyranoside), x is 6 (n-heptyl-β-D-glucopyranoside), x is 7 (n-octyl-β-D-glucopyranoside), x is 8 (n-nonyl-β-D-glucopyranoside), x is 9 (n-decyl-β-D-glucopyranoside), and x is 11 (n-dodecyl-β-D-glucopyranoside). Sometimes glucopyranosides are called glucosides. Exemplary alkyl glycosides additionally include those in which $R_1$ is maltose, R is $CH_3$, and x is 5 (n-hexyl-β-D-maltopyranoside), x is 7 (n-octyl-β-D-maltopyranoside), x is 8 (n-nonyl-β-D-maltopyranoside), x is 9 (n-decyl-β-D-maltopyranoside), x is 10 (n-undecyl-β-D-maltopyranoside), x is 11 (n-dodecyl-β-D-maltopyranoside), x is 12 (n-tridecyl-β-D-maltopyranoside), x is 13 (n-tetradecyl-β-D-maltopyranoside), and x is 15 (n-hexadecyl-β-D-maltopyranoside). Sometimes maltopyranosides are called maltosides. Exemplary alkyl glycosides further include those in which $R_1$ is glucose, x is 3, and R is cyclohexyl (3-cyclohexyl-1-propyl-β-D-glucoside); and in which $R_1$ is maltose, x is 4, and R is cyclohexyl (4-cyclohexyl-1-butyl-β-D-maltoside).

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cyloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo[2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amine, substituted amines, cyclic amines and basic ion exchange resins, [e.g., $N(R')_4+$ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and/or salts include histidine, succinate and acetate.

A "lyoprotectant" is a molecule which, when combined with a protein of interest, significantly prevents or reduces physicochemical instability of the protein upon lyophilization and subsequent storage. Exemplary lyoprotectants include sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; Pluronics®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred lyoprotectant are the non-reducing sugars trehalose or sucrose.

The lyoprotectant is added to the pre-lyophilized formulation in a "lyoprotecting amount" which means that, following lyophilization of the protein in the presence of the lyoprotecting amount of the lyoprotectant, the protein essentially retains its physicochemical stability upon lyophilization and storage.

A "pharmaceutically acceptable sugar" is a molecule which, when combined with a protein of interest, significantly prevents or reduces physicochemical instability of the protein upon storage. When the formulation is intended to be lyophilized and then reconstituted, "pharmaceutically acceptable sugars" may also be known as a "lyoprotectant". Exemplary sugars and their corresponding sugar alcohols includes: an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; Pluronics®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose.

Pharmaceutically acceptable sugars are added to the formulation in a "protecting amount" (e.g., pre-lyophilization) which means that the protein essentially retains its physicochemical stability during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods for treating a subject with impaired fertility or a subject at risk for impaired fertility by increasing the level or activity of AMH in a subject. The present invention is based in part on the discovery that administration of AMH results in the accumulation of small immature follicles, thereby preventing follicle maturation and follicle depletion.

For example, in one embodiment, the invention provides a composition comprising AMH. In one embodiment, the composition comprises an amount of AMH that results in accumulation of immature follicles while not providing excessive AMH that may have negative implications on follicular development. For example, in one embodiment, the composition is configured for delivery of about 100 ng/day to about 44,000 ng/day AMH to the subject. In one embodiment, the composition is a pharmaceutical composition comprising AMH. For example, in one embodiment, the composition comprises AMH and a pharmaceutical carrier. In one embodiment, the composition comprises a composition for stabilization, wherein the composition for stabilization comprises a surfactant, a buffer, and a liquid medium, and has a pH from about 5 to about 8.

In one embodiment, the invention provides a method of treating a subject having impaired fertility or at risk for impaired fertility, comprising administering to the subject an effective amount of a composition which increases the level or activity of AMH in the subject. For example, in one embodiment, the method comprises administering AMH to the subject. For example, in certain embodiments, the invention relates to the treatment of a subject with diminished ovarian reserve (DOR) or premature ovarian aging, which is characterized by reduced number of follicles available for maturation and ovulation. Certain subjects with diminished ovarian reserve have a decreased level of AMH, which results in unchecked initiation of primordial follicle growth thereby resulting in a rapid depletion of follicles. Treatment of a subject with a diminished ovarian reserve or at risk for a diminished ovarian reserve with AMH slows the development of follicles, and in certain instances restores a natural level of AMH and AMH-producing follicles.

In certain embodiments, the invention relates to the treatment of a subject who is undergoing, or will undergo, a gonadotoxic treatment, for example chemotherapy, which may induce rapid or complete follicle depletion. Post-cancer-treatment "burnout" is a condition that occurs when cancer treatment kills currently developing follicles. The lack of pre-antral follicles results in greatly reduced AMH production. This low AMH level triggers a DOR-like condition as primordial follicles mature too quickly. Moreover, because the follicles mature too quickly, they do not produce enough AMH to slow the follicle maturation, creating a feedback loop. If not treated, this results in running out of primordial follicles as in DOR. AMH treatment can correct this, by restoring a normal rate of primordial follicle maturation as well as reinstating pre-antral follicles and AMH to normal levels. In certain embodiments, a subject can be treated with AMH prior to initiation of the gonadotoxic treatment. In one embodiment, the subject is treated with AMH concurrent to the gonadotoxic treatment. In one embodiment, the subject is treated with AMH after the conclusion of the gonadotoxic treatment.

In one embodiment, AMH is administered to the subject at a dose of about 10 ng/day to about 100,000 ng/day. In one embodiment, AMH is administered to the subject at a dose of about 50 ng/day to about 50,000 ng/day. In one embodiment, AMH is administered to the subject at a dose of about 100 ng/day to about 44,000 ng/day. In one embodiment, AMH is administered to the subject at a dose of about 22,000 ng/day to about 44,000 ng/day. In one embodiment, AMH is administered to the subject at a dose of about 22,000 ng/day, about 25,000 ng/day, about 30,000 ng/day, about 35,000 ng/day, about 40,000 ng/day or about 44,000 ng/day. In one embodiment, AMH is administered to the subject for about 1 day to about 180 days. In one embodiment, AMH is administered to the subject for about 10 days to about 120 days. In one embodiment, AMH is administered to the subject for about 30 days to about 90 days. In one embodiment, AMH is administered to the subject for about 30 days, about 40 days, about 50 days, about 60 days, about 70 days, about 90 days.

In one embodiment, the invention provides a method of increasing the yield of oocytes during controlled ovarian hyperstimulation (COH) or superovulation. It is demonstrated herein that pre-treatment of AMH in subjects receiving controlled ovarian hyperstimulation (superovulation) increases the yield of oocytes, which can be then used for subsequent intrauterine insemination, in vitro fertilization (IVF), or cryopreservation. The method comprises administering a composition that increases the level or activity of AMH in the subject for a period of time prior to COH. AMH treatment can be used to increase the number of oocytes harvested in an induced ovulation cycle. Induced ovulation cycles are generally used in fertility treatment such as oocyte harvesting for IVF. In normal ovulation, a cohort of pre-antral follicles enters the antral stage at the same time and, over the course of an ovulation cycle, one follicle generates a mature oocyte and the other follicles undergo atresia. In an exemplary COH or superovulation therapy, ovulation is induced by administering an agent to the subject that speeds up follicle maturation and cause more than one follicle to ovulate and produce an oocyte. Exemplary agents that are used in COH or superovulation include, but are not limited to gonadotropins, FSH, LH, clomiphene, selective estrogen-receptor modulators (SERM), or aromatase inhibitors.

Therefore, in certain instances, a subject can be treated with AMH prior to COH or superovulation. The AMH treatment will cause follicles to remain in the pre-antral follicle stage, resulting in an increased number of pre-antral follicles. When AMH treatment is stopped and ovulation is induced, all the small follicles mature and ovulate together, which will result in a substantial increase in the number of oocytes produced.

In one embodiment, AMH is administered to the subject at a dose of about 10 ng/day to about 100,000 ng/day. In one embodiment, AMH is administered to the subject at a dose of about 50 ng/day to about 50,000 ng/day. In one embodiment, AMH is administered to the subject at a dose of about 100 ng/day to about 44,000 ng/day. In one embodiment, AMH is administered to the subject at a dose of about 22,000 ng/day to about 44,000 ng/day. In one embodiment, AMH is administered to the subject at a dose of about 22,000 ng/day, about 25,000 ng/day, about 30,000 ng/day, about 35,000 ng/day, about 40,000 ng/day or about 44,000 ng/day. In one embodiment, AMH is administered to the subject daily for a first period of time, prior to superovulation induction. In one embodiment, AMH is administered to the subject for a first period of time of about 1 day to about 180 days. In one embodiment, AMH is administered to the subject for a first period of time of about 10 days to about 120 days. In one embodiment, AMH is administered to the subject for a first period of time of about 30 days to about 90 days. In one embodiment, AMH is administered to the subject for about 30 days, about 40 days, about 50 days, about 60 days, about 70 days, about 90 days. In one embodiment, AMH treatment is stopped for a second period of time, after AMH treatment and prior to superovulation induction. In one embodiment, the second period of time, between AMH treatment and superovulation induction, is about 0 days to about 50 days. In one embodiment, the second period of time, between AMH treatment and superovulation induction, is about 5 days to about 40 days. In one embodiment, the second period of time, between AMH treatment and superovulation induction, is about 10 days to about 30 days. In one embodiment, the second period of time, between AMH treatment and superovulation induction, is about 1 day, about 5 days, about 10 days, about 15 days, about 20 days, about 25 days, about 30 days, about 35 days, or about 40 days.

The present invention also relates to the discovery that, AMH stall of follicular development and inhibition of ovulation are mediated through induction of two miRNAs, miR-181a and miR-181b, which regulate various aspects of FSH signaling and follicular growth, ultimately affecting downstream gene expression and folliculogenesis Thus, the present invention provides methods and compositions for modulating folliculogenesis modulating the expression or activity of AMH or microRNAs that are upregulated or downregulated by AMH. For example, in one embodiment, the method of the invention comprises administering at least one therapeutic from the group including, but not limited to, AMH, an inhibitor of AMH and a modulator of a microRNA (miR). The modulator of the miR can target one or more miRs, including but not limited to miR-181-a, miR-181b, or a combination thereof.

It is demonstrated herein that miR-181a and miR-181b target acvr2A and ADCY9 and regulate FSH signaling. Therefore, in one embodiment, the miR-181a modulator affects acvr2A expression. In another embodiment, the modulator of miR181-b affects ADCY9 expression. In another embodiment, the miR modulators of the invention change FSH-stimulated intracellular cAMP levels.

In some cases, it is advantageous to decrease the amount or effects of AMH. For example, in women with polycystic ovary syndrome (PCOS) there is excessive follicle recruitment and arrest in the antral stage, resulting in impaired ovulation. These small follicles in PCOS produce high levels of AMH and thus, one treatment option is to decrease the effects of AMH. Therefore, in some embodiments, the subject has a disease, disorder or syndrome characterized by increased levels of AMH. In one embodiment, the disease disorder or syndrome, includes but is not limited to PCOS.

In some embodiments, decreasing the amount or effects of AMH in a subject can be accomplished by administering an effective amount of an AMH inhibitor or an inhibitor of miR-181a or miR-181b. In one embodiment, inhibitor includes, but is not limited to, an siRNA, a ribozyme, an antisense, an aptamer, a peptidomimetic, an antibody, a peptide, a small molecule, and combinations thereof.

In other instances, it is advantageous to increase the amount or effects of AMH. For example, in women having decreased AMH, the initiation of primordial follicle growth becomes unchecked and follicles are lost faster than normal, resulting in pathophysiological conditions such as DOR, POA, POI and infertility. Therefore, in some embodiments, the subject has a disease, disorder or syndrome characterized by low levels of AMH. In one embodiment, the disease disorder or syndrome, includes but is not limited to DOR, POA, POI and infertility.

In some embodiments, increasing the amount or effects of AMH in a subject can be accomplished by administering an effective amount of AMH or an activator of miR-181a or miR-181b thereby increasing the expression or activity of miR-181a or miR-181b. In one embodiment, the activator includes, but is not limited to small molecule, a chemical compound, a protein, a peptide, a peptidomemetic, a nucleic acid, and combinations thereof.

The invention also provides compositions for modulating folliculogenesis. In one embodiment, the composition of the invention comprises an inhibitor of a microRNA (miR), wherein the miR is selected from the group consisting of miR-181a, miR-181b and a combination thereof. In another embodiment, the composition further comprises a pharmaceutically acceptable carrier. In one embodiment, the inhibitor is selected from the group consisting of an siRNA, a ribozyme, an antisense, an aptamer, a peptidomimetic, a small molecule, and combinations thereof.

Compositions

The invention provides a composition for increasing the level and/or activity of AMH in a subject. In certain embodiments, the composition may comprise a peptide, nucleic acid, small molecule, or any other agent which can increase the level and/or activity of AMH in a subject.

The invention also provides a composition for modulating folliculogenesis. In one embodiment, the composition increases the activity of one or more downstream targets of AMH, including but not limited to miR-181a and miR-181b. Exemplary compositions that increase the activity of miR-181a or miR-181b, include a small molecule, a chemical compound, a protein, a peptide, a peptidomemetic, a nucleic acid, and combinations thereof. In one embodiment, the composition comprises miR-181a, miR-181b, or a combination thereof.

In certain embodiments, the composition may comprise a miR inhibitor, including an inhibitor of miR-181a or an inhibitor of miR-181b. In some embodiments, the inhibitor can be an siRNA, a ribozyme, an antisense, an aptamer, a peptidomimetic, a peptide, an antibody, a small molecule, and combinations thereof. In certain embodiments, the miR inhibitor increases the expression of acvr2A, ADCY9, or both. In some instances, the miR inhibitor increases the FSH-stimulated intra-cellular cyclic AMP levels.

Peptides

In one embodiment, the composition comprises AMH protein, including for example isolated AMH or recombinant AMH. In certain embodiments, the composition comprises a biologically active fragment of AMH. In one embodiment, the composition comprises a biologically active homolog of AMH. In one embodiment, the composition comprises an isolated nucleic acid encoding AMH, fragment of AMH, or homolog of AMH.

The amino acid sequence of human AMH is provided below:

```
                                              (SEQ ID NO: 1)
MRDLPLTSLA LVLSALGALL GTEALRAEEP AVGTSGLIFR

EDLDWPPGSP QEPLCLVALG GDSNGSSSPL RVVGALSAYE

QAFLGAVQRA RWGPRDLATF GVCNTGDRQA ALPSLRRLGA

WLRDPGGQRL VVLHLEEVTW EPTPSLRFQE PPPGGAGPPE

LALLVLYPGP GPEVTVTRAG LPGAQSLCPS RDTRYLVLAV

DRPAGAWRGS GLALTLQPRG EDSRLSTARL QALLFGDDHR

CFTRMTPALL LLPRSEPAPL PAHGQLDTVP FPPPRPSAEL

EESPPSADPF LETLTRLVRA LRVPPARASA PRLALDPDAL

AGFPQGLVNL SDPAALERLL DGEEPLLLLL RPTAATTGDP

APLHDPTSAP WATALARRVA AELQAAAAEL RSLPGLPPAT

APLLARLLAL CPGGPGGLGD PLRALLLLKA LQGLRVEWRG

RDPRGPGRAQ RSAGATAADG PCALRELSVD LRAERSVLIP

ETYQANNCQG VCGWPQSDRN PRYGNHVVLL LKMQVRGAAL

ARPPCCVPTA YAGKLLISLS EERISAHHVP NMVATECGCR
```

In one embodiment, the composition comprises a peptide comprising an amino acid sequence of SEQ ID NO: 1. In one embodiment, the composition comprises a peptide comprising a biologically active fragment of the amino acid sequence of SEQ ID NO: 1. In one embodiment, the composition comprises a peptide comprising a biologically active homolog of the amino acid sequence of SEQ ID NO: 1. In one embodiment, the composition comprises an isolated nucleic acid encoding a peptide of the invention. For example, in one embodiment, the composition comprises an isolated nucleic acid encoding a peptide comprising an amino acid sequence SEQ ID NO: 1.

In one embodiment, the invention includes variants of the peptides of the invention. In one embodiment, variants differ from naturally-occurring peptides by conservative amino acid sequence differences or by modifications which do not affect sequence, or by both. For example, conservative amino acid changes may be made, which although they alter the primary sequence of the peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

In one embodiment, the peptide of the invention comprises a peptide comprising an amino acid sequence having at least 75% homology with the amino acid sequence of SEQ ID NO: 1. In one embodiment, the peptide of the invention comprises a peptide comprising an amino acid sequence having at least 80% homology with the amino acid sequence of SEQ ID NO: 1. In one embodiment, the peptide of the invention comprises a peptide comprising an amino acid sequence having at least 85% homology with the amino acid sequence of SEQ ID NO: 1. In one embodiment, the peptide of the invention comprises a peptide comprising an amino acid sequence having at least 90% homology with the amino acid sequence of SEQ ID NO: 1. In one embodiment, the peptide of the invention comprises a peptide comprising an amino acid sequence having at least 95% homology with the amino acid sequence of SEQ ID NO: 1. In one embodiment, the peptide of the invention comprises a peptide comprising an amino acid sequence having at least 98% homology with the amino acid sequence of SEQ ID NO: 1. In one embodiment, the peptide of the invention comprises a peptide comprising an amino acid sequence having at least 99% homology with the amino acid sequence of SEQ ID NO: 1.

In a further embodiment, the peptide of the invention comprise D-, L-, and unnatural isomers of amino acids. In one embodiment, the composition comprises a peptide comprising one or more unnatural or non-natural amino acids. Non-natural amino acids include, but are not limited to, the D-amino acids, 2,4-diaminobutyric acid, α-amino isobutyric acid, 2-aminoisobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, naphthalene, L-1-naphthalene, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general.

As known in the art the "similarity" between two peptides is determined by comparing the amino acid sequence and its conserved amino acid substitutes of one polypeptide to a sequence of a second peptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

In certain embodiments, the peptides of the invention comprise an N-terminal and/or C-terminal modifications that in certain instances improve activity. The present invention encompasses variants of the peptide analogs, including those with terminal modifications, without terminal modifications, or having different terminal modifications.

Variants of suitable peptides of the invention can also be expressed. Variants may be made by, for example, the deletion, addition, or alteration of amino acids that have either (i) minimal influence on certain properties, secondary structure, and hydropathic nature of the polypeptide or (ii) substantial effect on one or more properties of the peptide mimetics of the invention.

Variants may also include, for example, a peptide conjugated to a linker or other sequence for ease of synthesis, purification, identification, or therapeutic use (i.e., delivery) of the peptide.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the amino-acylated tRNA. These reactions are referred to as post-aminoacylation modifications. For example, the epsilon-amino group of the lysine linked to its cognate tRNA (tRNA$_{LYS}$), could be modified with an amine specific photoaffinity label.

The peptides of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide of the invention.

Cyclic derivatives of the peptides the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Peptides of the invention may also have modifications. Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties or to render them more suitable as a therapeutic agent. Such variants include those containing residues other than naturally-occurring L-amino acids, e.g., D-amino acids or non-naturally-occurring synthetic amino acids. The peptides of the invention may further be conjugated to non-amino acid moieties that are useful in their therapeutic application. In particular, moieties that improve the stability, biological half-life, water solubility, and/or immunologic characteristics of the peptide are useful. A non-limiting example of such a moiety is polyethylene glycol (PEG).

Covalent attachment of biologically active compounds to water-soluble polymers is one method for alteration and control of biodistribution, pharmacokinetics, and often, toxicity for these compounds (Duncan et al., 1984, Adv. Polym. Sci. 57:53-101). Many water-soluble polymers have been used to achieve these effects, such as poly(sialic acid), dextran, poly(N-(2-hydroxypropyl)methacrylamide) (PHPMA), poly(N-vinylpyrrolidone) (PVP), poly(vinyl alcohol) (PVA), poly(ethylene glycol-co-propylene glycol), poly(N-acryloyl morpholine (PAcM), and poly(ethylene glycol) (PEG) (Powell, 1980, Polyethylene glycol. In R. L. Davidson (Ed.) Handbook of Water Soluble Gums and Resins. McGraw-Hill, New York, chapter 18). PEG possess an ideal set of properties: very low toxicity (Pang, 1993, J. Am. Coll. Toxicol. 12: 429-456) excellent solubility in aqueous solution (Powell, supra), low immunogenicity and antigenicity (Dreborg et al., 1990, Crit. Rev. Ther. Drug Carrier Syst. 6: 315-365). PEG-conjugated or "PEGylated" protein therapeutics, containing single or multiple chains of polyethylene glycol on the protein, have been described in the scientific literature (Clark et al., 1996, J. Biol. Chem. 271: 21969-21977; Hershfield, 1997, Biochemistry and immunology of poly(ethylene glycol)-modified adenosine deaminase (PEG-ADA). In J. M. Harris and S. Zalipsky (Eds) Poly(ethylene glycol): Chemistry and Biological Applications. American Chemical Society, Washington, D.C., p 145-154; Olson et al., 1997, Preparation and characterization of poly(ethylene glycol)ylated human growth hormone antagonist. In J. M. Harris and S. Zalipsky (Eds) Poly(ethylene glycol): Chemistry and Biological Applications. American Chemical Society, Washington, D.C., p 170-181).

A peptide of the invention may be synthesized by conventional techniques. For example, the peptides of the invention may be synthesized by chemical synthesis using solid phase peptide synthesis. These methods employ either solid or solution phase synthesis methods (see for example, J. M. Stewart, and J. D. Young, Solid Phase Peptide Synthesis, 2$^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.)

The peptides may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purities, i.e., purities sufficient for research, diagnostic or therapeutic purposes.

Solid phase peptide synthesis is described by Stewart et al. in Solid Phase Peptide Synthesis, 2nd Edition, 1984, Pierce Chemical Company, Rockford, Ill.; and Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group, such as formation into a carbodiimide, a symmetric acid anhydride, or an "active ester" group, such as hydroxybenzotriazole or pentafluorophenyl esters.

Examples of solid phase peptide synthesis methods include the BOC method which utilized tert-butyloxycarbonyl as the alpha-amino protecting group, and the FMOC method which utilizes 9-fluorenylmethyloxycarbonyl to protect the alpha-amino of the amino acid residues, both which methods are well-known by those of skill in the art.

Incorporation of N- and/or C-blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function, e.g. with DCC, can then proceed by addition of the desired alcohol, followed by deprotection and isolation of the esterified peptide product.

The peptides of the invention may be prepared by standard chemical or biological means of peptide synthesis. Biological methods include, without limitation, expression of a nucleic acid encoding a peptide in a host cell or in an in vitro translation system.

Included in the invention are nucleic acid sequences that encode the peptide of the invention. In one embodiment, the invention includes nucleic acid sequences encoding a peptide comprising the amino acid sequence of SEQ ID NO: 1. Accordingly, subclones of a nucleic acid sequence encoding a peptide of the invention can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (2012), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity.

Biological preparation of a peptide of the invention involves expression of a nucleic acid encoding a desired peptide. An expression cassette comprising such a coding sequence may be used to produce a desired peptide for use in the method of the invention.

In the context of an expression vector, the vector can be readily introduced into a host cell, e.g., mammalian, bacterial, yeast or insect cell by any method in the art. Coding sequences for a desired peptide of the invention may be codon optimized based on the codon usage of the intended host cell in order to improve expression efficiency as demonstrated herein. Codon usage patterns can be found in the literature (Nakamura et al., 2000, Nuc Acids Res. 28:292). Representative examples of appropriate hosts include bacterial cells, such as streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The expression vector can be transferred into a host cell by physical, biological or chemical means, discussed in detail elsewhere herein.

Examples of biological methods to prepare the peptides of the present invention may utilize methods provided in published US Patent application number US 2009/0069241, which is incorporated herein in its entirety.

To ensure that the peptide obtained from either chemical or biological synthetic techniques is the desired peptide, analysis of the peptide composition can be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Nucleic Acids and Vectors

In one embodiment, the present invention provides a composition comprising an isolated nucleic acid encoding AMH, or a fragment thereof. In one embodiment, the isolated nucleic acid encodes a peptide comprising an amino acid sequence of SEQ ID NO: 1. Further, the invention encompasses an isolated nucleic acid encoding a peptide having substantial homology to a peptide disclosed herein. In certain embodiments, the isolated nucleic acid sequence encodes a peptide having at least 75%, 80%, 85%, 90%, 95%, 96%, 97%, 98%, or 99% sequence homology with an amino acid sequence of SEQ ID NO: 1.

In one embodiment, the composition comprises miR-181a, miR-181b, or a combination thereof. In another embodiment, the composition comprises an isolated nucleic acid molecule encoding miR-181a, miR-181b, or a combination thereof.

The isolated nucleic acid may comprise any type of nucleic acid, including, but not limited to DNA and RNA. For example, in one embodiment, the composition comprises an isolated DNA molecule, including for example, an isolated cDNA molecule, encoding a peptide of the invention, or functional fragment thereof. In one embodiment, the composition comprises an isolated RNA molecule encoding a peptide of the invention, or a functional fragment thereof. The isolated nucleic acids may be synthesized using any method known in the art.

The nucleic acid molecules of the present invention can be modified to improve stability in serum or in growth medium for cell cultures. Modifications of the nucleic acid of the invention may be present at one or more of, a phosphate group, a sugar group, backbone, N-terminus, C-terminus, or nucleobase. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, $NHR$, $NR_2$ or ON, wherein R is $C_1$-$C_6$ alkyl, alkenyl or alkynyl and halo is F, Cl, Br or I.

The present invention also includes a vector in which the isolated nucleic acid of the present invention is inserted. The art is replete with suitable vectors that are useful in the present invention.

In brief summary, the expression of natural or synthetic nucleic acids encoding a peptide is typically achieved by operably linking a nucleic acid encoding the peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of the peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention includes a composition comprising a cell which comprises a peptide of the invention, a nucleic acid encoding a peptide of the invention, or a combination thereof. In one embodiment, the cell is genetically modified to comprise a peptide and/or nucleic acid of the invention. In certain embodiments, genetically modified cell is autologous to a subject being treated with the composition of the invention. Alternatively, the cells can be allogeneic, syngeneic, or xenogeneic with respect to the subject. In certain embodiment, the cell is able to secrete or release the expressed peptide of the invention into extracellular space in order to deliver the peptide to one or more other cells.

The genetically modified cell may be modified in vivo or ex vivo, using techniques standard in the art. Genetic modification of the cell may be carried out using an expression vector or using a naked isolated nucleic acid construct.

In one embodiment, the cell is obtained and modified ex vivo, using an isolated nucleic acid encoding a peptide. In one embodiment, the cell is obtained from a subject, genetically modified to express the peptide and/or nucleic acid, and is re-administered to the subject. In certain embodiments, the cell is expanded ex vivo or in vitro to produce a population of cells, wherein at least a portion of the population is administered to a subject in need.

In one embodiment, the cell is genetically modified to stably express the peptide. In another embodiment, the cell is genetically modified to transiently express the peptide.

The present invention provides a scaffold or substrate composition comprising a peptide of the invention, an isolated nucleic acid of the invention, a cell comprising the peptide of the invention, or a combination thereof. For example, in one embodiment, a peptide of the invention, an isolated nucleic acid of the invention, a cell producing the peptide of the invention, or a combination thereof is incorporated within a scaffold. In another embodiment, a peptide of the invention, an isolated nucleic acid of the invention, a cell producing the peptide of the invention, or a combination thereof is applied to the surface of a scaffold. The scaffold of the invention may be of any type known in the art. Non-limiting examples of such a scaffold includes a, hydrogel, electrospun scaffold, foam, mesh, sheet, patch, and sponge.

Modulators of AMH, miR-181a, or miR-181b Expression and Activity

In one embodiment, the invention includes a modulator of AMH, miR-181a, or miR-181b expression or activity. In some embodiments, the modulator of AMH, miR-181a, or miR-181b expression or activity is an inhibitor. An inhibitor of AMH, miR-181a, or miR-181b expression or activity is any compound, molecule, or agent that inhibits AMH, miR-181a, or miR-181b expression or activity. An AMH, miR-181a, or miR-181b inhibitor may be an siRNA, a ribozyme, an antisense, an aptamer, a peptidomimetic, a small molecule, antibodies, peptides, or any combination thereof.

In some embodiments, the AMH inhibitor decreases the expression of miR-181a, miR-181b, or both. In one embodiment, the miR inhibitor increases the expression of ADCY9 or acvr2A. In one embodiment, the inhibitor of miR-181a increases the expression of acvr2A. In another embodiment, the inhibitor of miR-181b increases the expression of ADCY9. In yet another embodiment, the inhibitor of miR-181a or miR-181b increases FSH-stimulated intra-cellular cAMP levels.

In some embodiments, the modulator of AMH, miR-181a, or miR-181b expression or activity is an activator. An activator of AMH, miR-181a, or miR-181b expression or activity is any compound, molecule, or agent that increases AMH, miR-181a, or miR-181b expression, activity, or a combination thereof.

It will be understood by one skilled in the art, based upon the disclosure provided herein, that an increase in the level of AMH or a miR of the invention encompasses the increase in AMH or miR expression, including transcription and/or translation. The skilled artisan will also appreciate, once armed with the teachings of the present invention, that an increase in the level of AMH or the miR includes an increase in AMH or miR activity (e.g., targeting acvr2A or ADCY9). Thus, increasing the level or activity of AMH, miR-181a, or miR-181b includes, but is not limited to, increasing the amount of AMH, miR-181a, or miR-181b includes increase transcription or translation; and it also includes increasing any activity of AMH, miR-181a, or miR-181b as well.

(1) Nucleic Acids

In one embodiment, the present invention provides a composition comprising a nucleic acid inhibitor of AMH, miR-181a, or miR-181b. In one embodiment, the nucleic acid inhibitor is an siRNA or an antisense inhibitor. In some embodiments, the present invention provides a composition comprising an nucleic acid activator of AMH, miR-181a, or miR-181b.

siRNA

In one embodiment, siRNA is used to decrease the level of AMH, miR-181a, or miR-181b. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of miR-181a or miR-181b using RNAi technology.

In other related aspects, the invention includes an isolated nucleic acid encoding an inhibitor, wherein an inhibitor such as an siRNA or antisense molecule, inhibits AMH, miR-181a, or miR-181b, a derivative thereof, a regulator thereof, or a downstream effector, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein. In another aspect of the invention, AMH, miR-181a or miR-181b, or a regulator thereof, can be inhibited by way of inactivating and/or sequestering AMH, miR-181a or miR-181b, or a regulator thereof.

In another aspect, the invention includes a vector comprising an siRNA or antisense polynucleotide. Preferably, the siRNA or antisense polynucleotide is capable of inhibiting the expression of AMH or a target miR, wherein the target miR is selected from the group consisting of miR-181a or miR-181b, and downstream effectors, or regulators thereof. The incorporation of a desired polynucleotide into a vector and the choice of vectors is well-known in the art as described in, for example, Sambrook et al., supra, and Ausubel et al., supra, and elsewhere herein.

The siRNA or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA or antisense polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Modification of siRNA

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

Antisense Nucleic Acids

In one embodiment of the invention, an antisense nucleic acid sequence which is expressed by a plasmid vector is used to inhibit miR-181a or miR-181b expression or activity. The antisense expressing vector is used to transfect a mammalian cell or the mammal itself, thereby causing reduced endogenous expression of miR-181a or miR-181b.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

(2) Ribozymes

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit AMH, miR-181a, or miR-181b expression or activity. Ribozymes useful for inhibiting the expression or activity of a target molecule may be designed by incorporating target sequences into the basic ribozyme structure which are complementary, for example, to the sequence of AMH, miR-181a or miR-181b of the present invention. Ribozymes targeting AMH, miR-181a or miR-181b, may be synthesized using commercially available reagents (Applied Biosystems, Inc., Foster City, Calif.) or they may be genetically expressed from DNA encoding them.

(3) Small Molecules

When the AMH, miR-181a or miR-181b inhibitor is a small molecule, a small molecule agonist may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

(4) Antibodies

In another aspect of the invention, one or more of AMH, miR-181a or miR-181b can be inhibited by way of inactivating and/or sequestering the AMH, miR-181a or miR-181b. An antibody specific for the AMH, miR-181a or miR-181b may be used. In one embodiment, the antibody is a protein and/or compound having the desirable property of interacting with a binding partner of the target (e.g., AMH, miR-181a or miR-181b) and thereby competing with the corresponding protein. In another embodiment, the target (e.g., AMH, miR-181a or miR-181b) is a protein and/or compound having the desirable property of interacting with the target and thereby sequestering the target.

As will be understood by one skilled in the art, any antibody that can recognize and bind to an antigen of interest is useful in the present invention. Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magenetic-actived cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')$_2$ fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Treatment Methods

The present invention provides a method of treating a subject with impaired fertility or a subject at risk for impaired fertility. In certain embodiments, the method comprises administering to the subject an effective amount of a composition described herein to increase the level and/or activity of AMH in the subject. In certain embodiments, the method comprises administering to the subject an effective amount of a composition described herein to increase the level and/or activity of downstream effector of AMH, including but not limited to miR-181a or miR-181b.

In certain embodiments, the method is used to treat a subject with DOR, premature ovarian aging, or other condition characterized by a diminished level of follicles available for ovulation. A subject may be diagnosed as having DOR or related condition using methods known in the art. For example, in certain instances, DOR can be diagnosed by detecting a decreased level of AMH or inhibin B. In one embodiment, DOR can be diagnosed by detecting an elevated level of FSH or estradiol. In one embodiment, DOR can be diagnosed by determining antricle follicle count (AFC), for example by transvaginal ultrasonography. As described elsewhere herein, administration of AMH to a subject results in the accumulation of small immature follicles thereby preventing the depletion of follicles. Thus, in certain instances, the method comprises administering AMH, miR-181a, miR-181b, or a combination thereof to prevent ovulation until desired by the subject.

In certain embodiments, the method comprises delivery of AMH, miR-181a, miR-181b, or a combination thereof to a subject who will undergo, is currently undergoing, or has undergone gonadotoxic treatment. For example, AMH, miR-181a, miR-181b, or a combination thereof can be used on such subjects in order to prevent depletion of follicles that may result from gonadotoxic treatment. Exemplary gonadotoxic treatments include, but are not limited to, chemotherapy, radiation, ovarian surgery, and certain drugs known to deplete ovarian reserve. In certain embodiments, treatment is conducted prior to the gonadotoxic therapy. In one embodiment, treatment is conducted concurrent to the gonadotoxic therapy. In one embodiment, treatment is conducted following the gonadotoxic therapy.

In one embodiment, AMH is administered to the subject at a dose of about 10 ng/day to about 100,000 ng/day. In one embodiment, AMH is administered to the subject at a dose of about 50 ng/day to about 50,000 ng/day. In one embodiment, AMH is administered to the subject at a dose of about 100 ng/day to about 44,000 ng/day. In one embodiment, AMH is administered to the subject at a dose of about 22,000 ng/day to about 44,000 ng/day. In one embodiment, AMH is administered to the subject at a dose of about 22,000 ng/day, about 25,000 ng/day, about 30,000 ng/day, about 35,000 ng/day, about 40,000 ng/day or about 44,000 ng/day. In one embodiment, AMH is administered to the subject for about 1 day to about 180 days. In one embodiment, AMH is administered to the subject for about 10 days to about 120 days. In one embodiment, AMH is administered to the subject for about 30 days to about 90 days. In one embodiment, AMH is administered to the subject for about 30 days, about 40 days, about 50 days, about 60 days, about 70 days, about 90 days.

In one embodiment, the invention provides a method of increasing the yield of oocytes during controlled ovarian hyperstimulation (COH) or superovulation. The method comprises administering a composition described herein to increase the level and/or activity of AMH, miR-181a, miR-181b, or a combination thereof prior to COH. For example, as described elsewhere herein, pre-treatment of AMH for a period of time, followed by a period of time where AMH treatment is stopped, followed by COH/superovulation results in an increase in the yield of oocytes as compared to COH/superovulation alone. Thus, the present method provides for increasing the yield of oocytes induced by COH/superovulation which can then be used for subsequent intrauterine insemination, in vitro fertilization (IVF), or cryopreservation.

COH or superovulation can be performed on the subject using any method known in the art. For example, in an exemplary COH or superovulation therapy, ovulation is induced by administering an agent to the subject that speeds up follicle maturation and cause more than one follicle to ovulate and produce an oocyte. Exemplary agents that are used in COH or superovulation include, but are not limited to gonadotropins, FSH, LH, clomiphene, selective estrogen-receptor modulators (SERM), or aromatase inhibitors. AMH pretreatment will cause follicles to remain in the pre-antral follicle stage, resulting in an increased number of pre-antral follicles. When AMH treatment is stopped and ovulation is induced, all the small follicles mature and ovulate together, which will result in a substantial increase in the number of oocytes produced.

In one embodiment, AMH is administered to the subject at a dose of about 10 ng/day to about 100,000 ng/day. In one embodiment, AMH is administered to the subject at a dose of about 50 ng/day to about 50,000 ng/day. In one embodiment, AMH is administered to the subject at a dose of about 100 ng/day to about 44,000 ng/day. In one embodiment, AMH is administered to the subject at a dose of about 22,000 ng/day to about 44,000 ng/day. In one embodiment, AMH is administered to the subject at a dose of about 22,000 ng/day, about 25,000 ng/day, about 30,000 ng/day, about 35,000 ng/day, about 40,000 ng/day or about 44,000 ng/day. In one embodiment, AMH is administered to the subject daily for a first period of time, prior to superovulation induction. In one embodiment, AMH is administered to the subject for a first period of time of about 1 day to about 180 days. In one embodiment, AMH is administered to the subject for a first period of time of about 10 days to about 120 days. In one embodiment, AMH is administered to the subject for a first period of time of about 30 days to about 90 days. In one embodiment, AMH is administered to the subject for about 30 days, about 40 days, about 50 days, about 60 days, about 70 days, about 90 days. In one embodiment, AMH treatment is stopped for a second period of time, after AMH treatment and prior to superovulation induction. In one embodiment, the second period of time, between AMH treatment and superovulation induction, is about 0 days to about 50 days. In one embodiment, the second period of time, between AMH treatment and superovulation induction, is about 5 days to about 40 days. In one embodiment, the second period of time, between AMH treatment and superovulation induction, is about 10 days to about 30 days. In one embodiment, the second period of time, between AMH treatment and superovulation induction, is about 1 day, about 5 days, about 10 days, about 15 days, about 20 days, about 25 days, about 30 days, about 35 days, or about 40 days.

The composition of the invention may be administered to the subject using any method known in the art. Exemplary pharmaceutical compositions and routes of administration are detailed elsewhere herein. In certain embodiments, the administration of one or more peptides of the invention comprises administering one or more peptides along with a drug delivery vehicle. The drug delivery vehicle may be a microparticle, nanoparticle, liposome, micelle, or other vehicle known in the art. The drug delivery vehicle may be administered locally into one or more regions of the eye or systemically.

The present invention encompasses treatment of any species of subject, including, but not limited to humans and other primates, mammals including commercial relevant mammals such as cattle, pigs, horses, sheep, cats, dogs, rats, and mice. It certain instances the method comprises delivery of species-specific AMH, miR-181a, miR-181b, or a combination thereof to the subject. In some embodiments, the method does not require the delivery of species-specific AMH, miR-181a, or miR-181b. Rather, in certain embodiments, AMH, miR-181a, or miR-181b that may not be specific to the species being treated can be administered and have the desired effect described herein.

Pharmaceutical Compositions and Formulations

The invention also encompasses the use of pharmaceutical compositions of the invention or salts thereof to practice the methods of the invention. Such a pharmaceutical composition may consist of at least one composition of the invention or a salt thereof in a form suitable for administration to a subject, or the pharmaceutical composition may comprise at least one composition of the invention or a salt thereof, and one or more pharmaceutically acceptable carriers, one or more additional ingredients, or some combination of these. The composition of the invention may be present in the pharmaceutical composition in the form of a physiologically acceptable salt, such as in combination with a physiologically acceptable cation or anion, as is well known in the art.

Formulations of the invention may optionally include pharmaceutically acceptable salts, buffers, surfactants, other excipients, carriers, diluents, and/or other formulation agents.

Exemplary pharmaceutically acceptable buffers include acetate (e.g. sodium acetate), succinate (such as sodium succinate), glutamic acid, glutamate, gluconate, histidine, citrate or other organic acid buffers. Exemplary buffer concentration can be from about 1 mM to about 200 mM, or from about 10 mM to about 60 mM, depending, for example, on the buffer and the desired tonicity (e.g. isotonic, hypertonic or hypotonic) of the formulation. Exemplary pHs include from about 4.5 to about 6.5, or from about 4.8 to about 5.5, or from about 4 to 6, or about 5 to 5.5, or about 5, greater than about 5, greater than about 5.5, greater than about 6, or greater than about 6.5.

Suitable diluents, other excipients, or carriers and other agents include, but are not limited to, antioxidants, coloring, flavoring and diluting agents, emulsifying agents, suspending agents, solvents, fillers, bulking agents, buffers, vehicles, diluents and/or pharmaceutical adjuvants. For example, a suitable vehicle may be, physiological saline solution, citrate buffered saline, or artificial CSF, possibly supplemented with other materials common in compositions for parenteral administration. Neutral buffered saline or saline mixed with serum albumin are further exemplary vehicles. Those skilled in the art would readily recognize a variety of buffers that could be used in the compositions, and dosage forms used in the invention. Typical buffers include, but are not limited to pharmaceutically acceptable weak acids, weak bases, or mixtures thereof. Exemplary buffer components are water soluble materials such as phosphoric acid, tartaric acids, lactic acid, succinic acid, citric acid, acetic acid, ascorbic acid, aspartic acid, glutamic acid, or salts thereof. Exemplary salts include inorganic and organic acids, or bases such as metals or amines, in exemplary concentrations such as about 50-200 mM, or 100-200 mM, or about 100 mM, or about 150 mM.

Other excipients or stabilizers may also be included, for example, sugars (e.g., sucrose, glucose, trehalose, fructose, xylose, mannitose, fucose), polyols (e.g., glycerol, mannitol, sorbitol, glycol, inositol), amino acids or amino acid derivatives, or surfactants (e.g., polysorbate, including polysorbate 20, or polysorbate 80, or poloxamer, including poloxamer 188). Exemplary concentrations of surfactant may range from about 0.001% to about 0.5%, or from about 0.003% to about 0.2%. Preservatives may also be included, such as benzyl alcohol, phenol, m-cresol, chlorobutanol or benzethonium Cl, e.g. at concentrations ranging from about 0.1% to about 2%, or from about 0.5% to about 1%.

One or more other pharmaceutically acceptable carriers, excipients or stabilizers such as those described in Remington's Pharmaceutical Sciences 21st edition, Osol, A. Ed. (2005) may be included in the formulation provided that they do not adversely affect the desired characteristics of the formulation.

In certain embodiments, the invention provides a formulation comprising AMH and a composition for stabilization. In other embodiments, the invention provides a formulation comprising an inhibitor of miR-181a or miR-181b. For example, in one embodiment, the composition for stabilization comprises a surfactant, a buffer, and a liquid medium, and has a pH from about 5 to about 8. Exemplary pharmaceutical formulations comprising peptides are described in the art, for example in U.S. Patent Application Publication No. US2014/0303357, the contents of which are incorporated herein by reference.

In certain embodiments, the invention provides an aqueous formulation comprising AMH, a miR-181a inhibitor, or a miR-181b inhibitor and a compound for reducing the viscosity of the formulation. For example, in certain embodiments, the formulation comprises a compound for reducing viscosity, such as certain charged amino acids or analogs thereof, including but not limited to, arginine (either arginine-HCl or arginine in the presence of a succinate counterion, e.g., arginine succinate), arginine dipeptide, arginine tripeptide, polyarginine, homoarginine, 2-amino-3-guanidino-propionic acid, guanidine, ornithine, agmatine, guanidobutyric acid, urea, citrulline, N-hydroxy-L-nor-arginine, nitroarginine methyl ester, argininamide, arginine methyl ester, arginine ethyl ester, lysine, lysinamide, lysine methyl ester, histidine, histidine methyl ester, histamine, alanine, alaninamide, alanine methyl ester, putrescine, cadaverine, spermidine, spermine, and methionine (U.S. Patent Application No. 2013/0058958). In certain embodiments, the formulation comprises a lyophilized powder comprising AMH and an excipient that reduces the viscosity upon reconstitution with a diluent. In other embodiments, the formulation comprises a lyophilized powder comprising a miR inhibitor. Exemplary excipients which can reduce the viscosity of a reconstituted formulation include, but is not limited to taurine, theanine, sarcosine, citrulline, betaine and mixtures thereof (U.S. Patent Application No. 2013/0171128).

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In certain embodiments, the AMH or miR inhibitor comprising pharmaceutical formulation of the invention may be formulated in either aqueous or lyophilized form, the latter being capable of being reconstituted into an aqueous form.

The formulations described herein may be prepared as reconstituted lyophilized formulations. The proteins described herein are lyophilized and then reconstituted to produce the liquid formulations of the invention. In this particular embodiment, after preparation of the protein of interest as described above (e.g., AMH), a "pre-lyophilized formulation" is produced. The amount of protein present in the pre-lyophilized formulation is determined taking into account the desired dose volumes, mode(s) of administration etc. For example, the starting concentration of an intact protein can be from about 2 mg/ml to about 50 mg/ml, preferably from about 5 mg/ml to about 40 mg/ml and most preferably from about 20-30 mg/ml.

The protein to be formulated is generally present in solution. For example, in the liquid formulations of the invention, the protein may be present in a pH-buffered solution at a pH from about 4-8, and preferably from about 5-7. The buffer concentration can be from about 1 mM to about 200 mM, alternatively from about 1 mM to about 100 mM, alternatively from about 1 mM to about 50 mM, alternatively from about 3 mM to about 15 mM, depending, for example, on the buffer and the desired tonicity of the formulation (e.g., of the reconstituted formulation). Exemplary buffers and/or salts are those which are pharmaceutically acceptable and may be created from suitable acids, bases and salts thereof.

In one embodiment, a lyoprotectant is added to the pre-lyophilized formulation. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. However, exemplary lyoprotectant concentrations in the pre-lyophilized formulation are from about 10 mM to about 400 mM, alternatively from about 30 mM to about 300 mM, alternatively from about 50 mM to about 100 mM. Exemplary lyoprotectants include sugars and sugar alcohols such as sucrose, mannose, trehalose, glucose, sorbitol, mannitol. However, under particular circumstances, certain lyoprotectants may also contribute to an increase in viscosity of the formulation. As such, care should be taken so as to select particular lyoprotectants which minimize or neutralize this effect.

The ratio of protein to lyoprotectant can vary for each particular protein and lyoprotectant combination. In certain embodiments, for generating an isotonic reconstituted formulation with a high protein concentration, the molar ratio of lyoprotectant to protein may be from about 100 to about 1500 moles lyoprotectant to 1 mole protein, and preferably from about 200 to about 1000 moles of lyoprotectant to 1 mole protein, for example from about 200 to about 600 moles of lyoprotectant to 1 mole protein.

A mixture of the lyoprotectant (such as sucrose or trehalose) and a bulking agent (e.g., mannitol or glycine) may be used in the preparation of the pre-lyophilization formulation. The bulking agent may allow for the production of a uniform lyophilized cake without excessive pockets therein etc. Other pharmaceutically acceptable carriers, excipients or stabilizers such as those described in *Remington's Pharmaceutical Sciences* 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

The formulation herein may also contain more than one protein as necessary for the particular indication being treated, preferably those with complementary activities that do not adversely affect the other protein. For example, it may be desirable to provide two or more proteins in a single formulation. Such proteins are suitably present in combination in amounts that are effective for the purpose intended.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, optional lyoprotectant and other optional components are mixed together, the formulation is lyophilized. Many different freeze-dryers are available for this purpose such as Hull50™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g., 40-60 hrs). Optionally, a secondary drying stage may also be performed depending upon the desired residual moisture level in the product. The temperature at which the secondary drying is carried out ranges from about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g., 10-15 hours). The pressure may be the same as that employed during the primary drying step. Freeze-drying conditions can be varied depending on the formulation and vial size.

Prior to administration to the patient, the lyophilized formulation is reconstituted with a pharmaceutically acceptable diluent such that the protein concentration in the reconstituted formulation is at least about 50 mg/ml, for example from about 50 mg/ml to about 400 mg/ml, alternatively from about 80 mg/ml to about 300 mg/ml, alternatively from about 90 mg/ml to about 150 mg/ml. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/ml, or from about 10-40 mg/ml protein in the reconstituted formulation). In certain embodiments, the protein concentration in the reconstituted formulation is significantly higher than that in the pre-lyophilized formulation. For example, the protein concentration in the reconstituted formulation may be about 2-40 times, alternatively 3-10 times, alternatively 3-6 times (e.g., at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWF), a pH buffered solution (e.g., phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are ≥10 µm in size.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, intraperitoneal, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea, octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, m-cresol and combinations thereof. A particularly preferred preservative is a combination of about 0.5% to 2.0% benzyl alcohol and 0.05% to 0.5% sorbic acid.

Tonicity agents, sometimes known as "stabilizers" are present to adjust or maintain the tonicity of a liquid composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Stability of the proteins described herein may be enhanced through the use of non-toxic "water-soluble polyvalent metal salts". Examples include $Ca^{2+}$, $Mg^{2+}$, $Zn^{2+}$, $Fe^{2+}$, $Fe^{3+}$, $Cu^{2+}$, $Sn^{2+}$, $Sn^{3+}$, $Al^{2+}$ and $Al^{3+}$. Example anions that can form water soluble salts with the above polyvalent metal cations include those formed from inorganic acids and/or organic acids. Such water-soluble salts have a solubility in water (at 20° C.) of at least about 20 mg/ml, alternatively at least about 100 mg/ml, alternative at least about 200 mg/ml.

Suitable inorganic acids that can be used to form the "water soluble polyvalent metal salts" include hydrochloric, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). For example, exemplary monocarboxylic acids within this definition include the saturated $C_2$-9 monocarboxylic acids acetic, proprionic, butyric, valeric, caproic, enanthic, caprylic pelargonic and capryonic, and the unsaturated $C_{2-9}$ monocarboxylic acids acrylic, propriolic methacrylic, crotonic and isocrotonic acids. Exemplary dicarboxylic acids include the saturated $C_{2-9}$ dicarboxylic acids malonic, succinic, glutaric, adipic and pimelic, while unsaturated $C_{2-9}$ dicarboxylic acids include maleic, fumaric, citraconic and mesaconic acids. Exemplary tricarboxylic acids include the saturated $C_{2-9}$ tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium proprionate, zinc glycolate, calcium lactate, zinc lactate and zinc tartrate); and (3) the aromatic carboxylic acid metal salts of benzoates (e.g., zinc benzoate) and salicylates.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as Arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as Arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or Arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount of a therapeutic composition of the invention. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, and the type and age of the animal.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

In some embodiments, the dose of a compound of the invention is from about 1 ng and about 100,000 ng. In some embodiments, a dose of a compound of the invention used in compositions described herein is less than about 100,000 ng, or less than about 80,000 ng, or less than about 60,000 ng, or less than about 50,000 ng, or less than about 30,000 ng, or less than about 20,000 ng, or less than about 10,000 ng, or less than about 5,000 ng, or less than about 2,000 ng, or less than about 500 ng and all whole or partial increments thereof.

In one embodiment, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects. Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. Microencapsulation of recombinant proteins for sustained release has been successfully performed with human growth hormone (rhGH), interferon-(rhIFN-), interleukin-2, and MN rpg 120. Johnson et al., *Nat. Med.* 2: 795-799 (1996); Yasuda et al., *Biomed. Ther.* 27: 1221-1223 (1993); Hora et al., *Bio/Technology* 8: 755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds., (Plenum Press: New York, 1995), pp. 439-462; WO 97/03692; WO 96/40072; WO 96/07399; and U.S. Pat. No. 5,654,010.

The sustained-release formulations of these proteins may be developed using poly lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer", in *Biodegradable Polymers as Drug Delivery Systems* (Marcel Dekker; New York, 1990), M. Chasin and R. Langer (Eds.) pp. 1-41.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

Routes of Administration

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Vaginal Administration

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Regulation of Follicular Development by AMH

Figure 2:
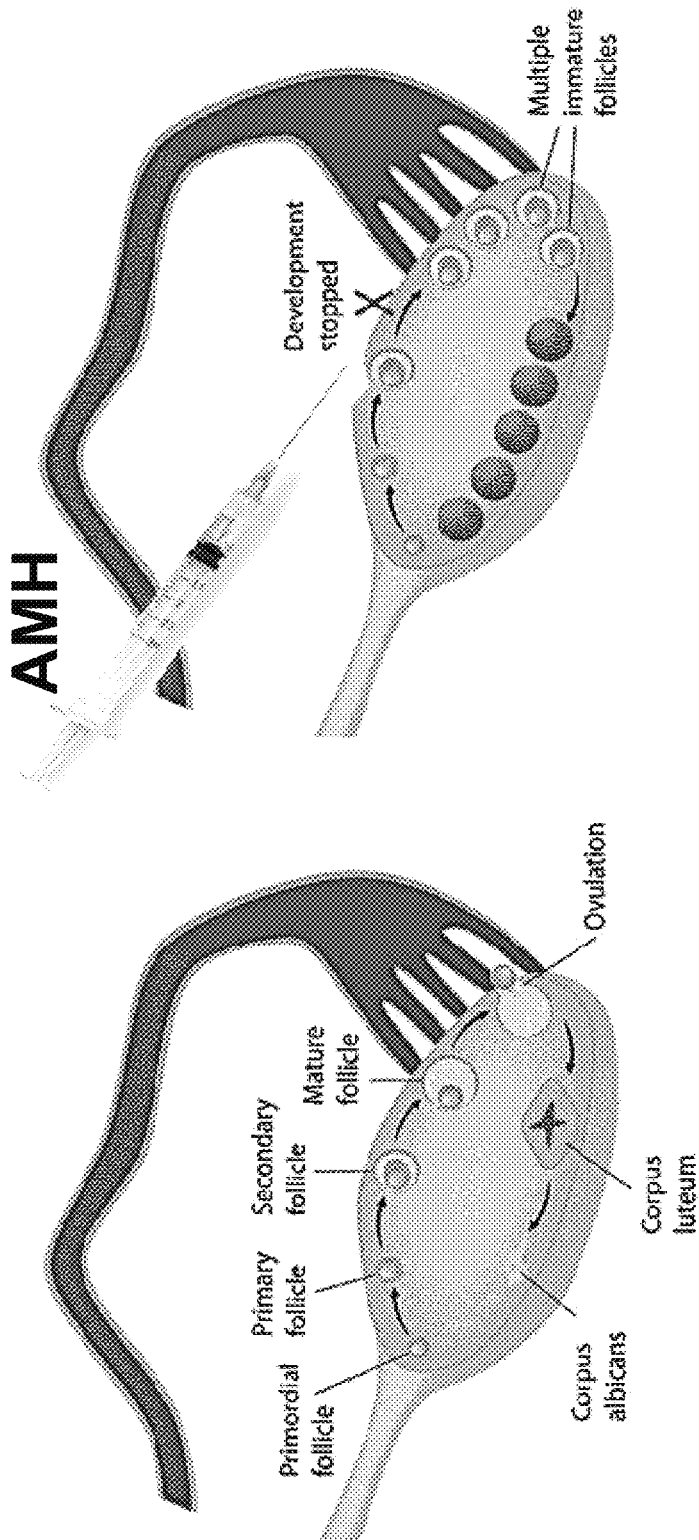
FIG. 2 is a schematic depicting the proposed effect of AMH on follicle development resulting in the accumulation of immature follicles.

The role of AMH across the female reproductive lifespan has only more recently come to light. Physiologically, AMH is a follicular gatekeeper limiting follicle growth initiation, and subsequently estradiol production from small antral follicles prior to selection. AMH is also considered an intra-ovarian regulator that inhibits follicular atresia. For example, as shown in FIG. 1, in AMH knockout mice, it was observed that more follicles grow, resulting in a decrease in primordial follicles and an increase in both small follicles and atretic follicles (Durlinger et al., 1999, Endocrinology, 140(12): 5789-96; Durlinger et al., 2001, Endocrinology, 142(11): 4891-9; Durlinger et al., 2002, Endocrinology 143(3): 1076-84; Durlinger et al., 2002, Reproduction, 124 (5): 601-9). Here using a mouse model, experiments were conducted to further define the role of AMH in follicular development. It was examined whether treatment with AMH blocked normal follicle development which would then result in an accumulation of immature follicles (FIG. 2).

The results of the experiments are now described.

In Vivo AMH Treatment Suppresses Follicular Development

Experiments were performed using 21 day old pre-pubertal mice and 8-9 week old mice. Pre-pubertal mice were treated daily for 4 weeks with either 120 ng or 300 ng AMH (intraperitoneal (IP) injection). The 8-9 week old mice were treated daily for 4 weeks with 300 ng of AMH (IP injection). Thereafter, ovaries were fixed, paraffin embedded and 5-mm sections were taken at 30 mm intervals, and subjected to hematoxylin and eosin staining for histological examination.

Figure 3A:
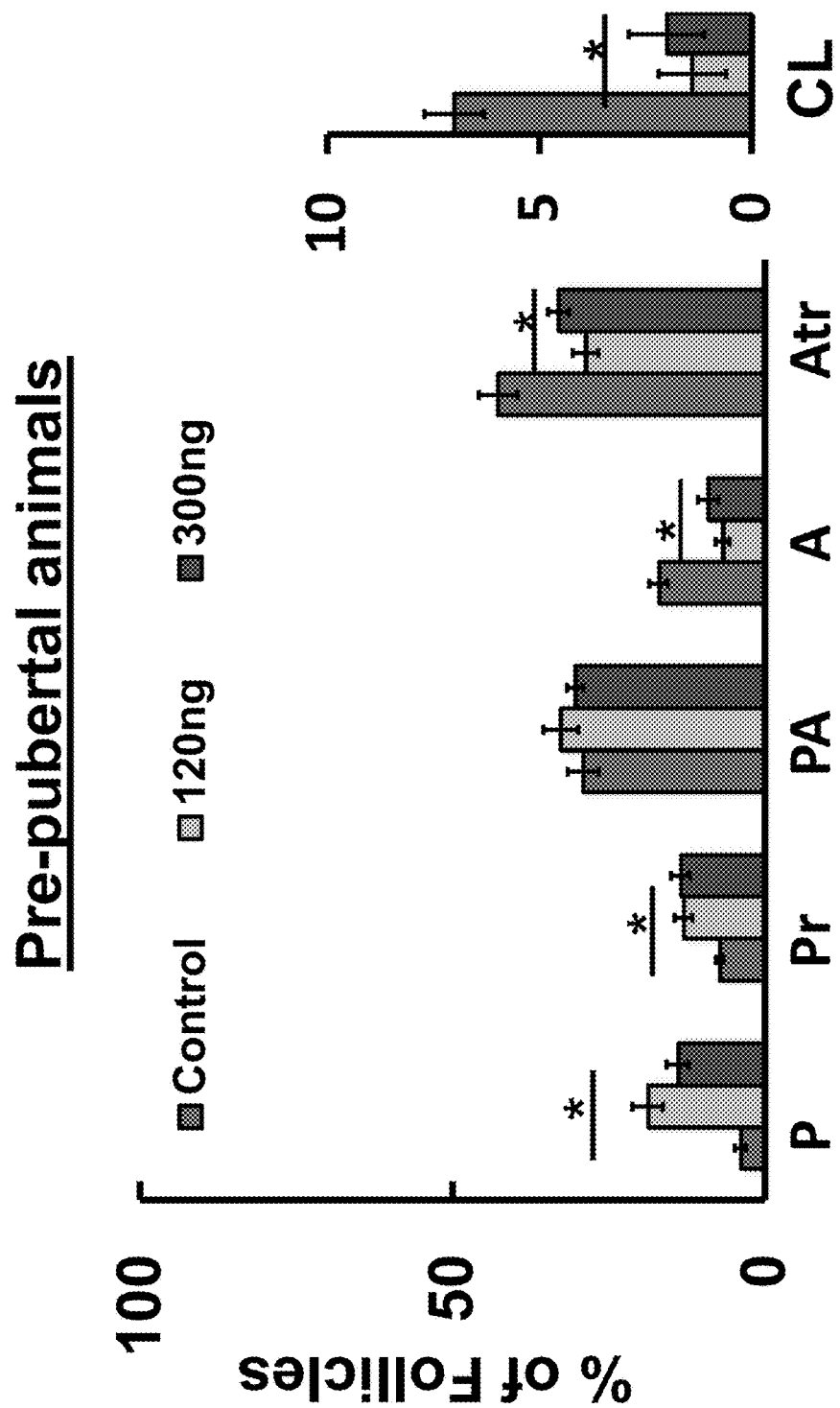
FIG. 3A through FIG. 3C, depicts the results of experiments where 21 day old pre-pubertal (FIG. 3A) and 8-9 week (FIG. 3B and FIG. 3C) old mice were treated daily for 4 weeks with 120/300 ng and 300 ng of AMH injections (IP), respectively. Thereafter, ovaries were fixed, paraffin embedded and 5-µm sections were taken at 30 m intervals, and subjected to hematoxylin and eosin staining for histological examination. Follicle (P-primordial; Pr-primary; PA-preantral; A-antral; Atr-atretic and CL-corpus luteum) numbers were evaluated as described previously (Sen et al., 2010, Mol Endocrinol, 24(7): 1393-403; Sen et al., 2014, Proc Natl Acad Sci USA, 111(8): 3008-13). The effect of AMH on follicle number is shown for pre-pubertal mice (FIG. 3A) and for 8-9 week old mice (FIG. 3A). For 8-9 weeks old mice, cycling patterns were determined by daily vaginal smears (FIG. 3B). n=5 and *P≤0.05

It was found that daily IP injection of AMH (120 ng and 300 ng) into pre-pubertal (21 d old) mice (5 animals/treatment) for 4 weeks increases the percentage of primordial and primary follicles, decreases antral and artretic follicles, but does not change pre-antral follicle counts compared to vehicle treated mice (FIG. 3A). Moreover, irrespective of the AMH dose, treated animals have significantly fewer corpora lutea than controls (FIG. 3A).

Figure 3B:
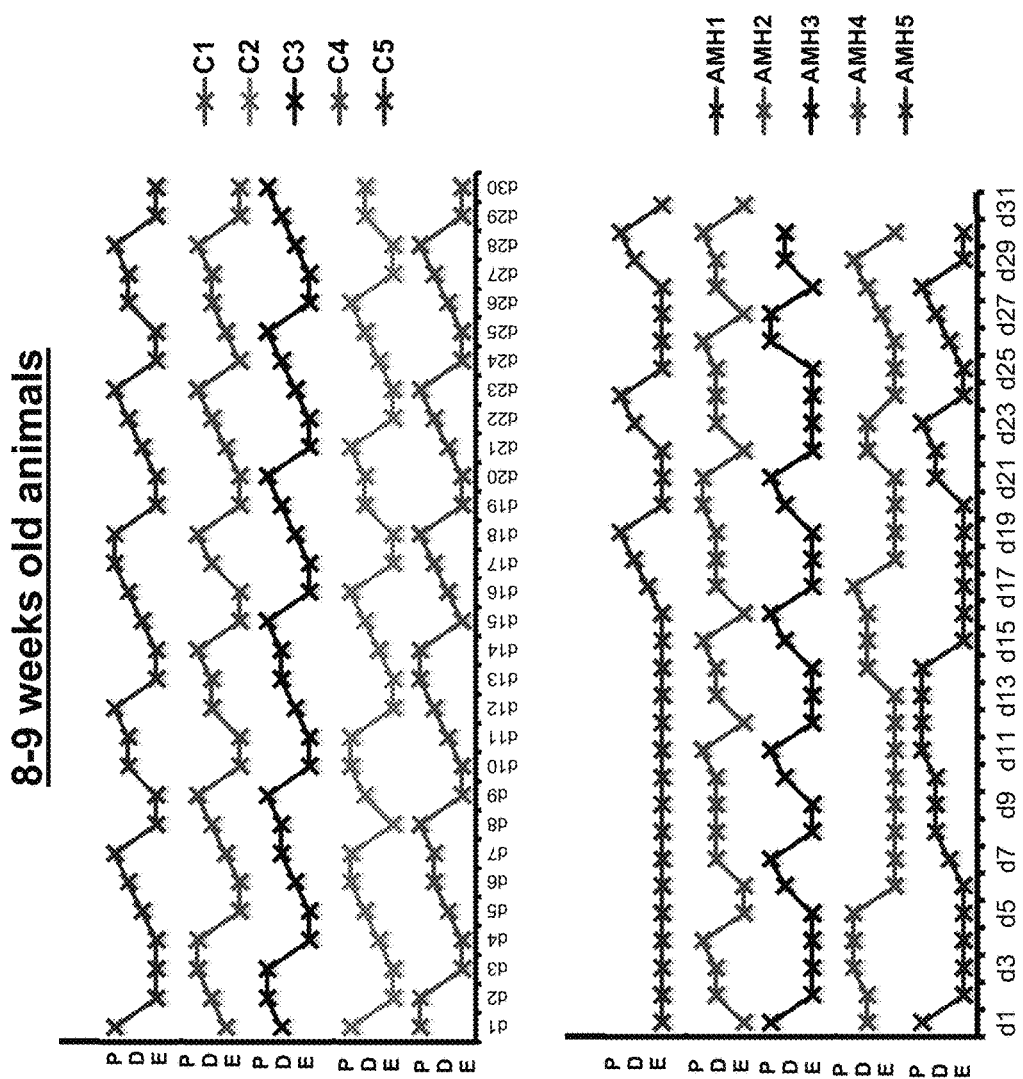
Figure 3C:
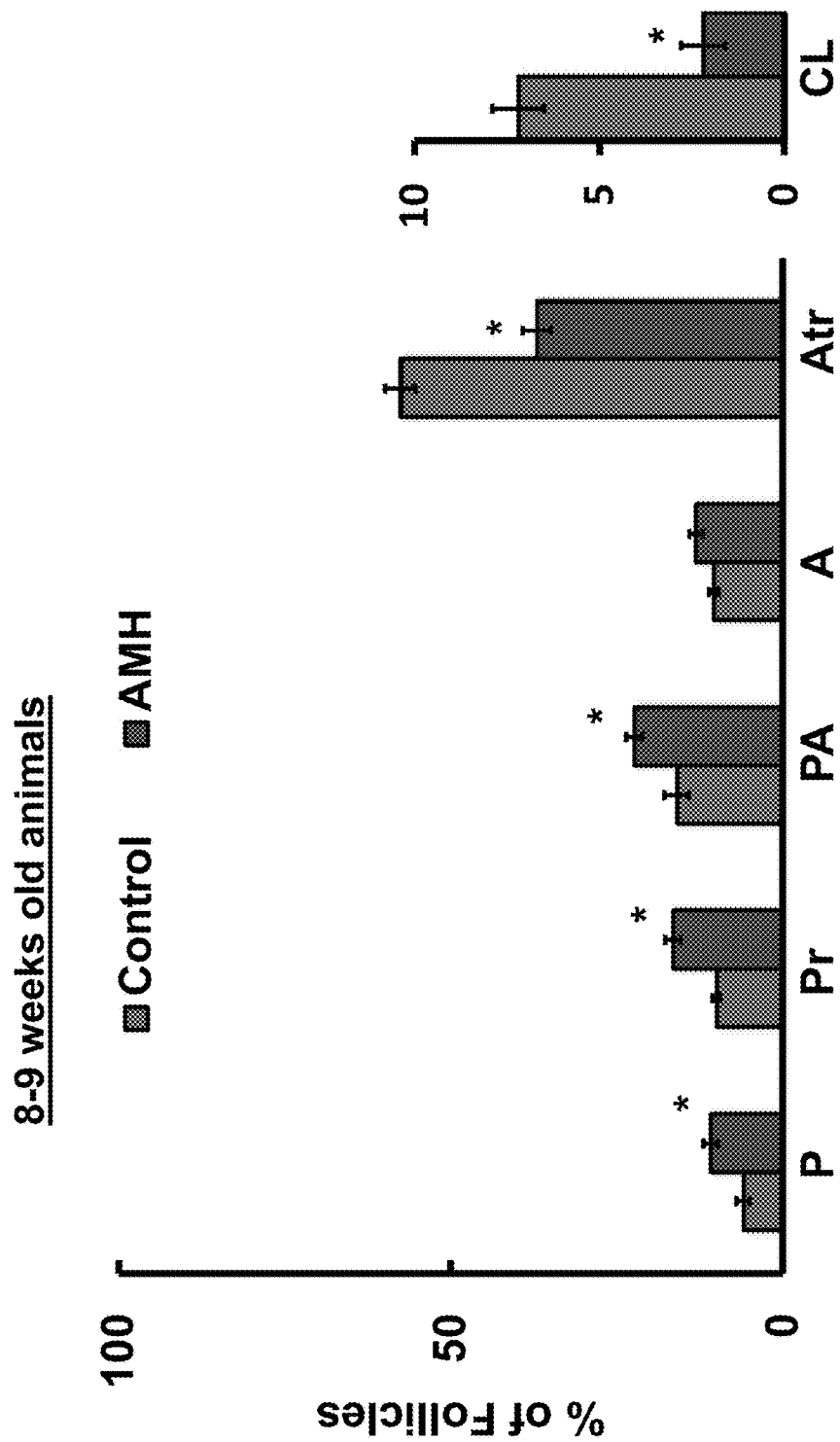

Similarly, AMH (300 ng) injections to 8-9 week old mice disrupt cycling (measured by daily vaginal smears) (FIG. 3B) and inhibit follicular development, with higher percentages of primordial, primary and pre-antral follicles, and lower atretic follicles and corpora lutea (FIG. 3C). These results suggest that AMH treatment impairs cycling and blocks follicular development. Since AMH receptors are expressed both in brain and ovaries, these AMH effects may be mediated either at the hypothalamus-pituitary axis or directly at the ovarian level. Studies are ongoing to differentiate the central and ovarian effects of AMH on follicular development.

Figure 4A:
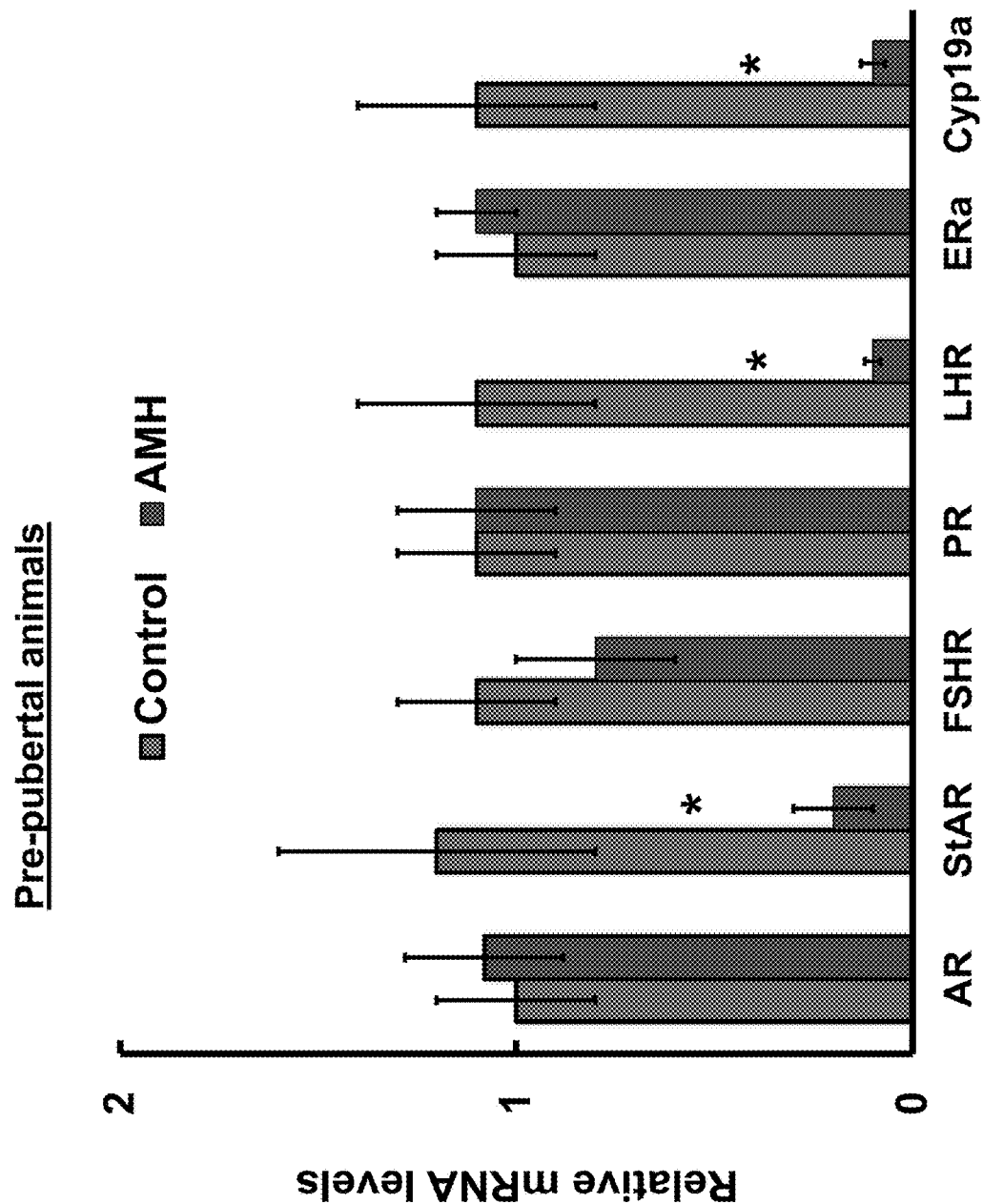
FIG. 4A and FIG. 4B, depicts the results of experiments where total RNA was isolated from ovaries of 21 d old pre-pubertal (FIG. 4A) and 8-9 weeks (FIG. 4B) old mice treated daily for 4 weeks with 300 ng of AMH injections (IP) and subjected to quantitative real-time PCR. Data was normalized to GAPDH and represented as ±SEM. n=5 and *P≤0.05
Figure 4B:
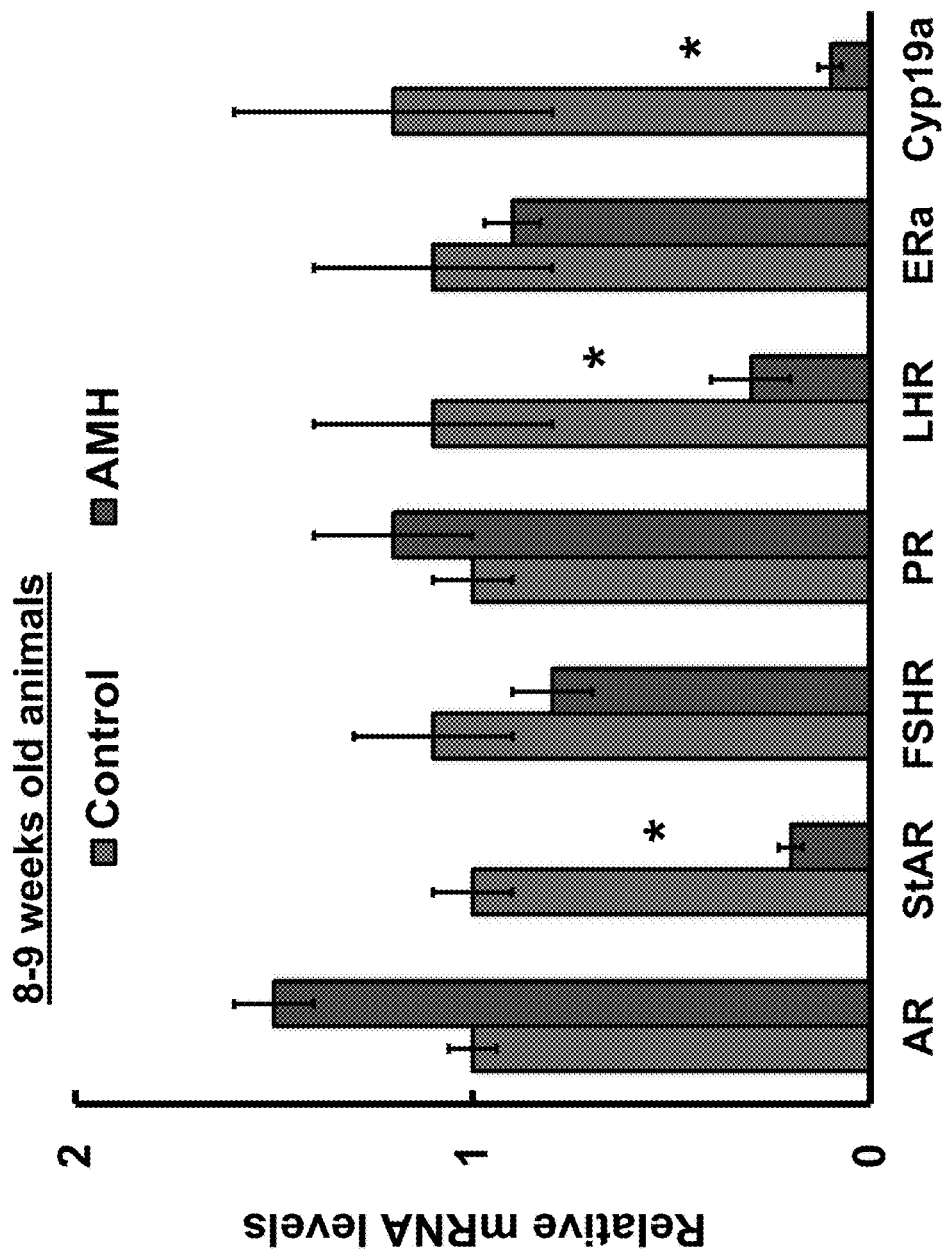

AMH-Induced Ovarian Gene Expression in Pre-Pubertal and Reproductive Aged Animals Experiments were conducted to determine if AMH administration altered the gene expression in treated mice. Total RNA was isolated from ovaries of 21 d old pre-pubertal and 8-9 weeks old mice treated daily for 4 weeks with 300 ng of AMH injections (IP) and subjected to quantitative real-time PCR. It was observed that the mRNA levels of stAR, LHR, and Cyp19a was reduced in both pre-pubertal mice (FIG. 4A) and in 8-9 week old mice (FIG. 4B). Intriguingly, it is found that in both pre-pubertal and 8-9 week old mice, AMH treatment significantly lowers steroidogenic acute regulator protein, Cyp19 and luteinizing hormone receptor mRNA levels in the ovary compared to controls (FIG. 4). Since these genes are all targets of FSH signaling, the present results are consistent with other studies that suggest that AMH antagonizes FSH effects.

Figure 5A:
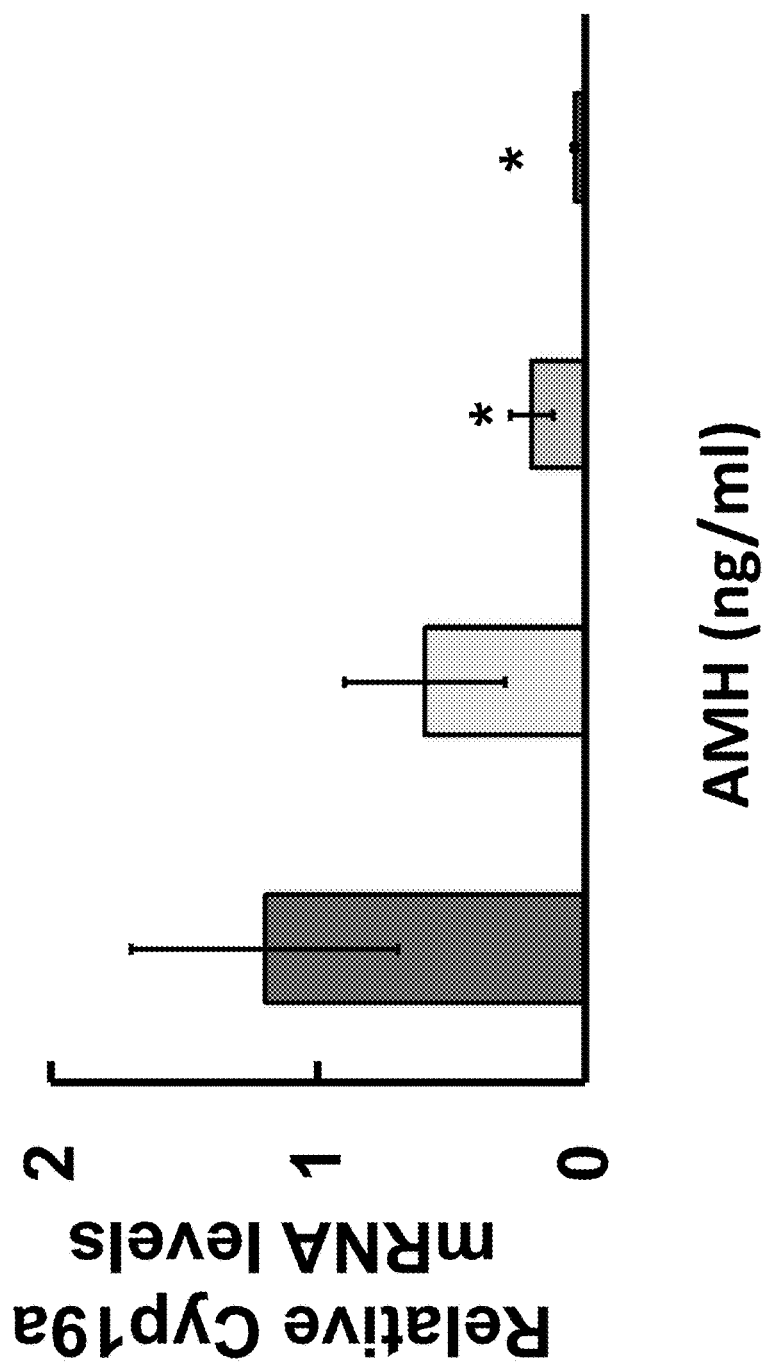
FIG. 5A and FIG. 5B, depicts the results of experiments evaluating the Cyp19a mRNA (FIG. 5A) and intracellular cAMP (FIG. 5B) levels in mouse primary granulosa cell cultures isolated from 8-9 weeks old animals treated with different concentrations of AMH for 18 h. Data is represented as ±SEM, n=3 and *P≤0.05
Figure 5B:
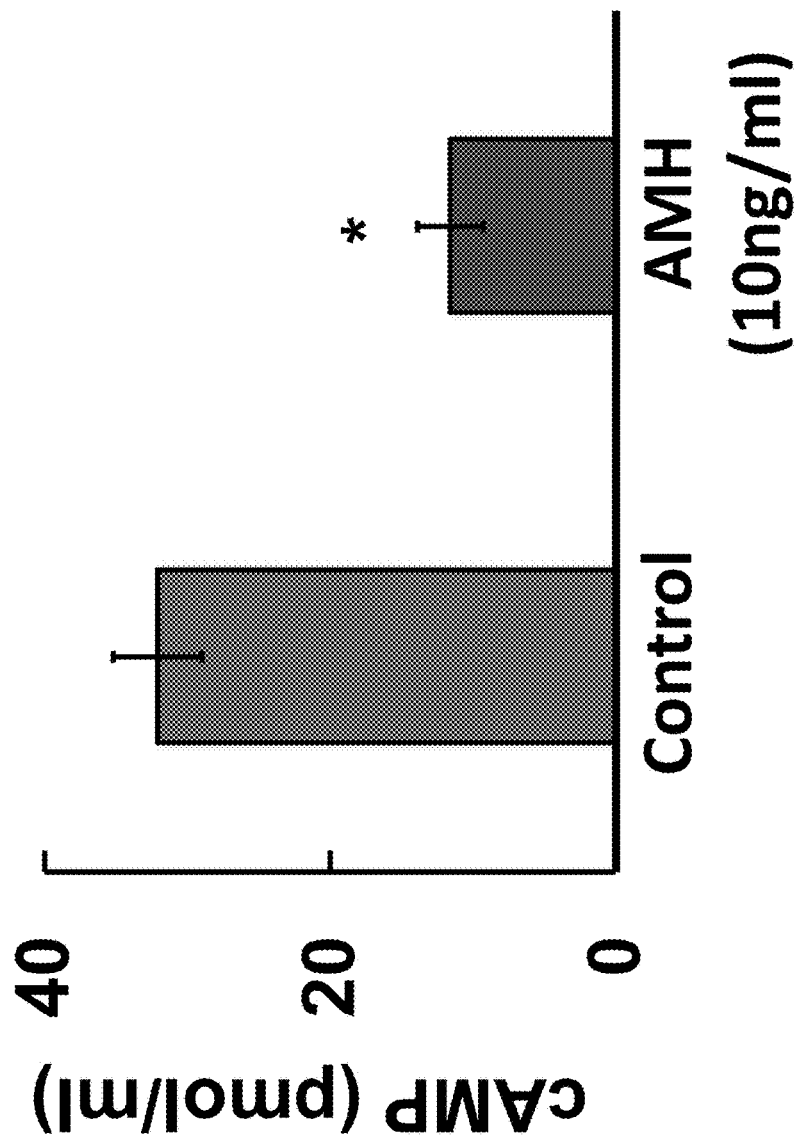

AMH Directly Inhibits Cyp19a Expression and Intracellular cAMP Levels in Mouse Primary Granulosa Cell Cultures Additional experiments were conducted using mouse primary granulosa cell cultures, to examine the effect of AMH on Cyp19a expression and intracellular cAMP levels. Granulosa cells (GCs) isolated form 8-9 week old animals were cultured in vitro and treated with different concentrations of AMH for 18 hours. It was observed that Cyp19a mRNA expression (FIG. 5A) and intracellular cAMP level (FIG. 5B) decreased after AMH treatment.

Inhibitory Effects of AMH are Mediated, at Least in Parts, by miR-181

Experiments were conducted to evaluate the role the effect of AMH on miR-181 both in vitro and in vivo. For the in vitro experiments, granulosa cells (GCs) isolated from 8-9 week animals were cultured and then treated with 10 ng/ml of AMH for 18 hours. For the in vivo experiments, ovaries were isolated from 8-9 weeks old mice after 4 weeks of daily AMH (300 ng) injections (IP).

Figure 6A:
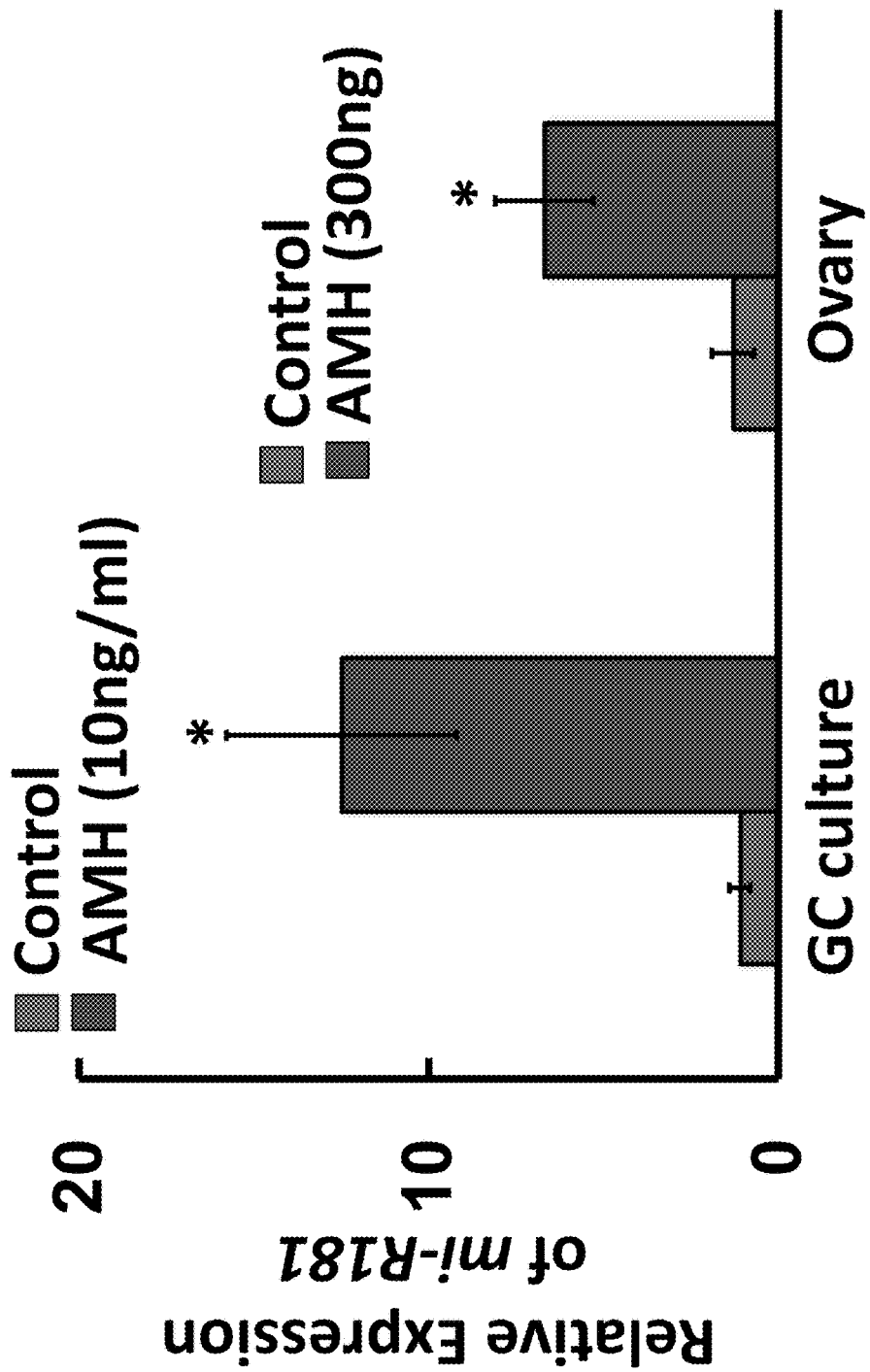
FIG. 6A and FIG. 6B, depicts the results of experiments demonstrating that the inhibitory effects of AMH are mediated, at least in part, by miR-181.
Figure 6B:
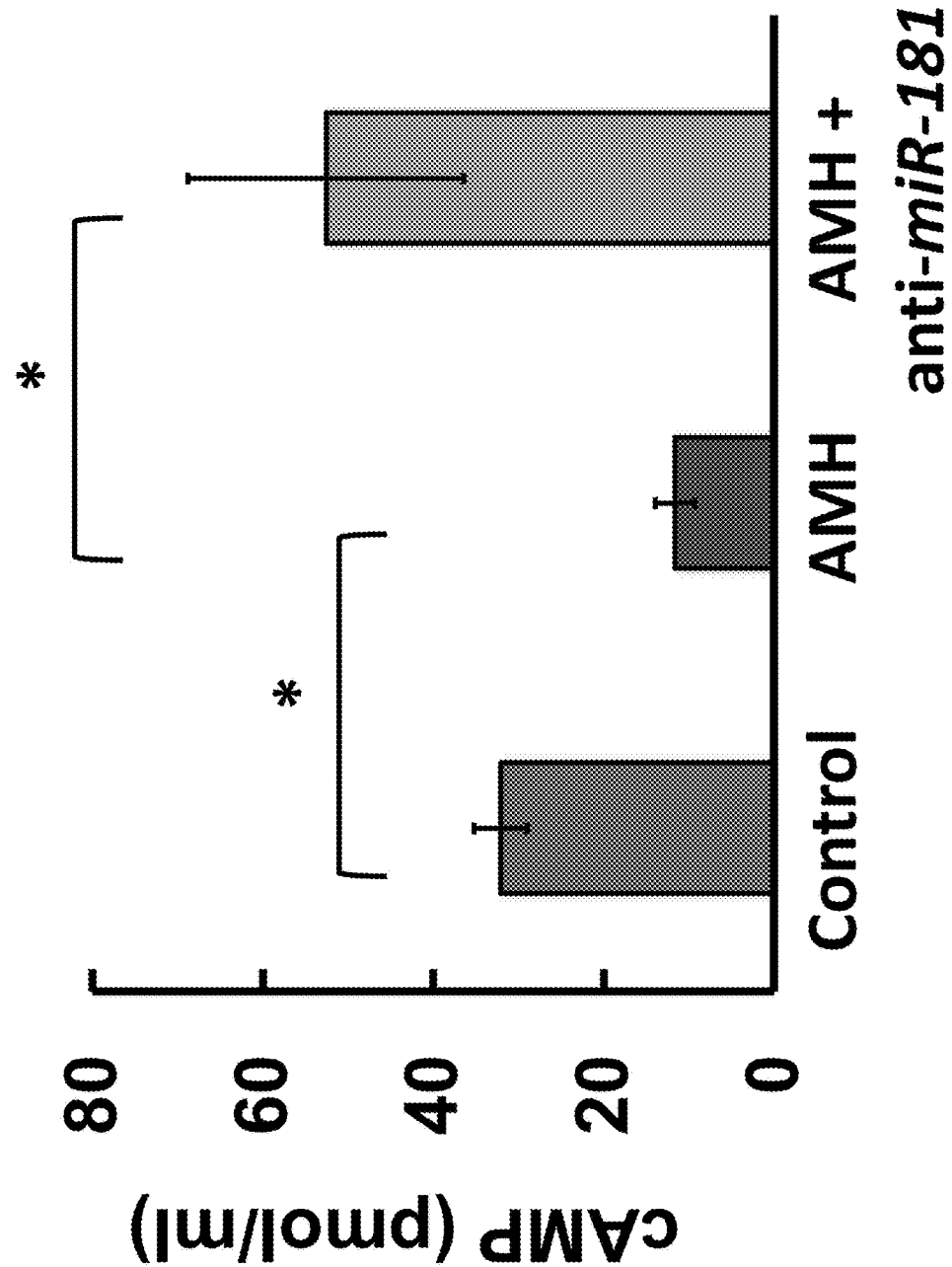

Interestingly it was found that a micro RNA, miR-181 is induced by AMH treatment both in vitro and in vivo (FIG. 6A). This microRNA targets adenylate cyclase 9 and cAMP response element-binding protein (CREB), both of which are essential components of FSH-cAMP signaling pathway that is critical for follicular development. Therefore, whether the inhibitory effects of AMH are mediated by miR-181 in GCs was examined. Since adenylate cyclase 9 is important for the formation of cAMP intracellular cAMP levels were measured in GCs treated with AMH in presence or absence of an inhibitor of miR-181. Results show that while AMH significantly decreases cAMP levels, anti-miR-181 treatment rescues this effect (FIG. 6B).

AMH Pre-Treatment May have a Positive Impact on Super-Ovulation

Figure 7:
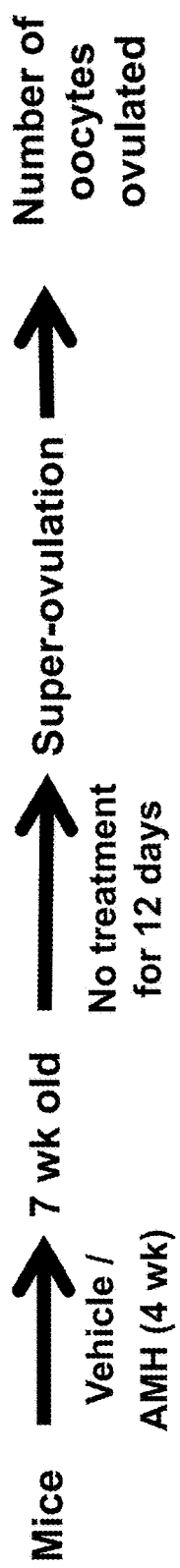
FIG. 7, comprising

Finally, given that AMH blocks complete follicular development, resulting in overall follicle accumulation, it was examined whether stopping AMH treatment followed by superovulation would increase the number of ovulated oocytes. Pre-pubertal and 8-9 week old mice were treated with AMH (300 ng) or vehicle for 4 weeks followed by 12 days of no treatment. Thereafter these animals were subjected to superovulation regime. For superovulation, mice were given a single IP injection of 5 U of pregnant mare serum gonadotropin (Sigma, St. Louis, Mo.) followed 48 hours later by 5 U of human chorionic gonadotropin (Sigma). After an additional 18 hours, oocyte/cumulus masses were surgically isolated from the oviduct and ampulla and counted as described previously (Sen et al., 2010, Mol Endocrinol, 24(7): 1393-403; Sen et al., 2014, Proc Natl Acad Sci USA, 111(8): 3008-13). Results show that irrespective of age, AMH treated animals super-ovulated more oocytes (pre-pubertal: 26±1.5 vs 18.3±0.9 (FIG. 7A); 8-9 week: 15±0.6 vs 20.3±0.9 (FIG. 7B)). These studies may provide insights into AMH effects on pathophysiological conditions like premature ovarian insufficiency and/or PCOS.

The data presented herein show that while AMH slows the development of follicles most likely, by inhibiting FSH actions and blocks ovulation, it also prevents follicular atresia. The inhibitory effect of AMH on FSH actions are mediated in parts by miR-181. Moreover, AMH pre-treatment increases the number of oocytes harvested in an induced ovulation cycle. Further studies are required to understand the intra-cellular mechanism of AMH and its physiological role in normal and pathophysiological conditions like diminished ovarian reserve or polycystic ovarian syndrome.

Example 2: Proposed Protocols for Administration of Anti-Müllerian Hormone (AMH) to Women and Girls Described herein are exemplary protocols for the treatment of female subjects using AMH. The average serum AMH is approximately 4 ng/ml in healthy young women with normal ovarian reserve (Kelsey et al., 2011, PLoS One, 6: e22024). The half-life of AMH is 27.6 hrs (Griesinger et al., 2012, The Journal of Clinical Endocrinology and Metabolism, 97: 2160-2163). The PCOS range is approximately 3 fold higher (Tal et al., 2014, American Journal of Obstetrics and Gynecology, 211:59: e51-58) while DOR is approximately 3 fold lower (Gleicher et al., 2010, Fertility and Sterility, 94: 2824-2827). The approximate time from primary follicle recruitment to ovulation is about 90-120 days (McGee et al., 2000, Endocrine Reviews, 21: 200-214.

For Women with Low Ovarian Reserve Who are Pursuing Controlled Ovarian Hyperstimulation (COH) for Fertility Treatment:

Pretreatment with AMH prior to COH is intended to improve follicular synchrony, oocyte yield and pregnancy rates with fertility treatments. Starting dose of AMH is 4 to 8 ng/ml daily×typical volume (5,500 ml)=22,000 to 44,000 ng/day for 90 days. Dose and duration may require adjustments based on future studies, patients size as well as other parameters. This treatment would be followed by a short washout period ranging from days to weeks. Followed by controlled ovarian hyperstimulation (superovulation) (commonly used agents include: gonadotropins, selective estrogen-receptor modulators, and aromatase inhibitors) followed by either Intrauterine Insemination or Oocyte Retrieval for In Vitro Fertilization or for Oocyte/Embryo cryopreservation.

For Women and Girls Who are Pursuing Fertility Preservation Due to Imminent Exposure to Gonadotoxic Treatments:

Treatment with AMH prior to and contemporaneously with gonadotoxic treatments is intended to decrease activation and recruitment of primordial follicles via a so-called "burnout" effect, which induces rapid and often complete loss of ovarian reserve via follicle depletion. Recruitment adds follicles to the pool of so-called growing follicles, which, in contrast to primordial follicles, are very sensitive to damage from chemotherapy drugs and/or radiotherapy (Kalich-Philosoph et al., 2013, Science Translational Medicine, 5: 185ra162.

By preventing follicle activation, AMH potentially protects the gonads from chemotherapy and radiation therapy by keeping follicles at primordial stages, where they are less sensitive to damage, thereby preventing loss of fertility as a consequence of gonadotoxic treatments, as currently seen in cancer patients and in other medical conditions requiring such treatments.

Starting dose of AMH is 4 to 8 ng/ml daily×typical adult volume (5,500 ml)=22,000 to 44,000 ng/day. Dose and duration may require adjustments based on future studies, patients size as well as other parameters. Lower doses may be appropriate for pediatric patients. Treatment with AMH is initiated several days prior and continued during gonadotoxic treatment, AMH should be continued until gonadotoxic treatment is stopped. In cases where gonadotoxic treatment has already been initiated AMH can be added as soon as clinically possible.

Furthermore, women who have developed low ovarian reserve due to gonadotoxic treatment may later benefit from the above outlined protocol for AMH pre-treatment prior to COH.

Example 3: Intra-Cellular Mechanism of Anti-Müllerian Hormone (AMH) in Regulation of Follicular Development Using a mouse model and a human GC cell line, this study describes an underlying mechanism of AMH actions that may account for some of the reported effects of AMH on follicular development. The results presented herein show that through induction of two miRNAs, miR-181a and miR-181b, AMH regulates various aspects of FSH signaling and follicular growth, which, ultimately, affects downstream gene expression and folliculogenesis. Further, the utilized mouse models AMH pre-treatment to superovulation improves oocyte yields. These data, therefore, offer new insights into the mechanism of AMH actions, and may explain reported negative effects of AMH on follicular development.

The materials and methods of the experiments are now described.

Animals and Cell Culture 21 d old pre-pubertal and 8-9 week old C57BL/6J mice (Jackson Laboratory) were subjected to daily intra-peritoneal (IP) injection of AMH (120 ng or 300 ng) or vehicle (5 animals/treatment) for 4 weeks. Estrous cycle was determined for the 8-9 week old animals throughout the course of treatment by vaginal smears, as described previously (Ma et al., 2016, Endocrinology en20151750; Sen and Hammes, 2010, Mol Endocrinol 24:1393-403). Thereafter, ovaries were isolated for morphological and gene expression studies and blood was collected to measure estradiol levels. Collection and culture of mouse GCs were performed as previously described (Ma et al., 2016, Endocrinology en20151750; Sen and Hammes, 2010, Mol Endocrinol 24:1393-403; Sen et al., 2014, PNAS 111:3008-13; Sen et al., 2012, J Clin Invest 122:2469-81). For both in vitro and in vivo studies, AMH treatment involved AMH recombinant protein (*E. Coli* derived) from MyBioSource (Cat# MBS968365).

Ovarian Morphology

For follicle counting, ovaries (n=5 ovaries from different animals/treatment) were paraffin-embedded, processed for sectioning (5 μm sections taken at 30 μm intervals) and stained with hematoxylin and eosin for morphological analysis using previously published criteria (Ma et al., 2016, Endocrinology en20151750; Sen and Hammes, 2010, Mol Endocrinol 24:1393-403). Briefly, follicle numbers were evaluated as: (1) primordial follicles—identified by an oocyte partially or completely encapsulated by flattened squamous cells; (2) primary follicles—single layer of cuboidal GCs around the oocyte; (3) secondary-tertiary follicles (pre-antral)—2 layers or more of cuboidal GC (no antrum); (4) antral follicles—presence of an antrum and (5) corpus luteum (CL). Follicles were considered atretic based on any of the two criteria: three or more pyknotic nuclei or atretic bodies (depending on the follicle type) in GC layers or follicular antrum, GCs pulling away from basement membrane, broken basement membrane, uneven GC layer, and non intact oocyte or nucleus. The data are represented as percentage of follicles.

In Vitro Follicle Culture

In vitro follicle culture was performed as described previously (Sen and Hammes, 2010, Mol Endocrinol 24:1393-403; Sen et al., 2014, PNAS 111:3008-13). Briefly, follicles of 120-150 μm size with two or three layers of GCs, an intact basal lamina, and few theca cells (approximately pre-antral follicles) were manually isolated from 21 d-old mice. 30 follicles were initially isolated from 5 different animals and 10 follicles were randomly assigned to each treatment group. The follicles were then cultured at 37° C. in a humidified atmosphere (5% CO2 and 95% air) for 4 d in DMEM supplemented with 5 μg/ml of insulin, 5 μg/ml of transferin, 5 ng/ml of sodium selenite, 1% penicillin-streptomycin, and 10 ng/ml of recombinant human FSH in presence or absence of AMH (5 and 10 ng/ml). The maximal follicle diameter at the beginning (D0) and end (D4) of culture was measured by using the morphometric tool of the Zeiss Axioplan microscope (Carl Zeiss, Inc., Thornwood, N.Y.). The data represented here are the average increase in diameter of 10 follicles/treatment.

RNA Extraction and Real Time PCR

RNA from ovaries or GCs was isolated using RNeasy Mini Kit (Qiagen, Valencia, Calif.) according to the manufacturer's instructions and levels of androgen receptor (AR), steroidogenic acute regulatory protein (StAR), follicle stimulating hormone receptor (FSHR), progesterone receptor (PR), luteinizing hormone receptor (LHR), estrogen receptor alpha (ERα), aromatase (Cyp19a1), activin receptor 2A (acvr2A), adenylate cyclase 9 (ADCY9) and GAPDH mRNA expression were analyzed by ΔΔ Ct method using Taqman gene expression assay primers (Assay ID # Mm00442688_m1-AR, Mm00441558_m1-StAR, Mm00442819_m1-F SHR, Mm00518647_m1-Ptgr2(PR), Mm00442931_m1-Lhcgr (LHR), Mm00433143_m1-Esrra (ERα), Mm00484049_m1-1 Cyp19a1, Mm00431657_m1-acvr2A, Mm00507743_m1-Adcy9 (ADCY9) and Mm03302249_g-GAPDH; Applied Biosystems) and ABI StepOne plus real-time PCR machine. 1 μg of RNA was used for all the RT-PCR reactions.

Estradiol Assay

Estradiol levels were measured by a 17beta Estradiol ELISA Kit (Abcam) with a detectable range of 20-2000 μg/ml as per the manufacturer's instructions (Ma et al., 2016, Endocrinology en20151750). The intra-assay coefficient of variation was 7.2%.

Cyclic AMP (cAMP) Assay

Intra-cellular cAMP levels were measured by cAMP competitive ELISA (Thermo Scientific) as per the manufacturer's instructions (Ma et al., 2016, Endocrinology en20151750). The intra-assay coefficient of variation was 6.6%.

miRNA Isolation and Detection

Figures 17A, 17B, 17C:
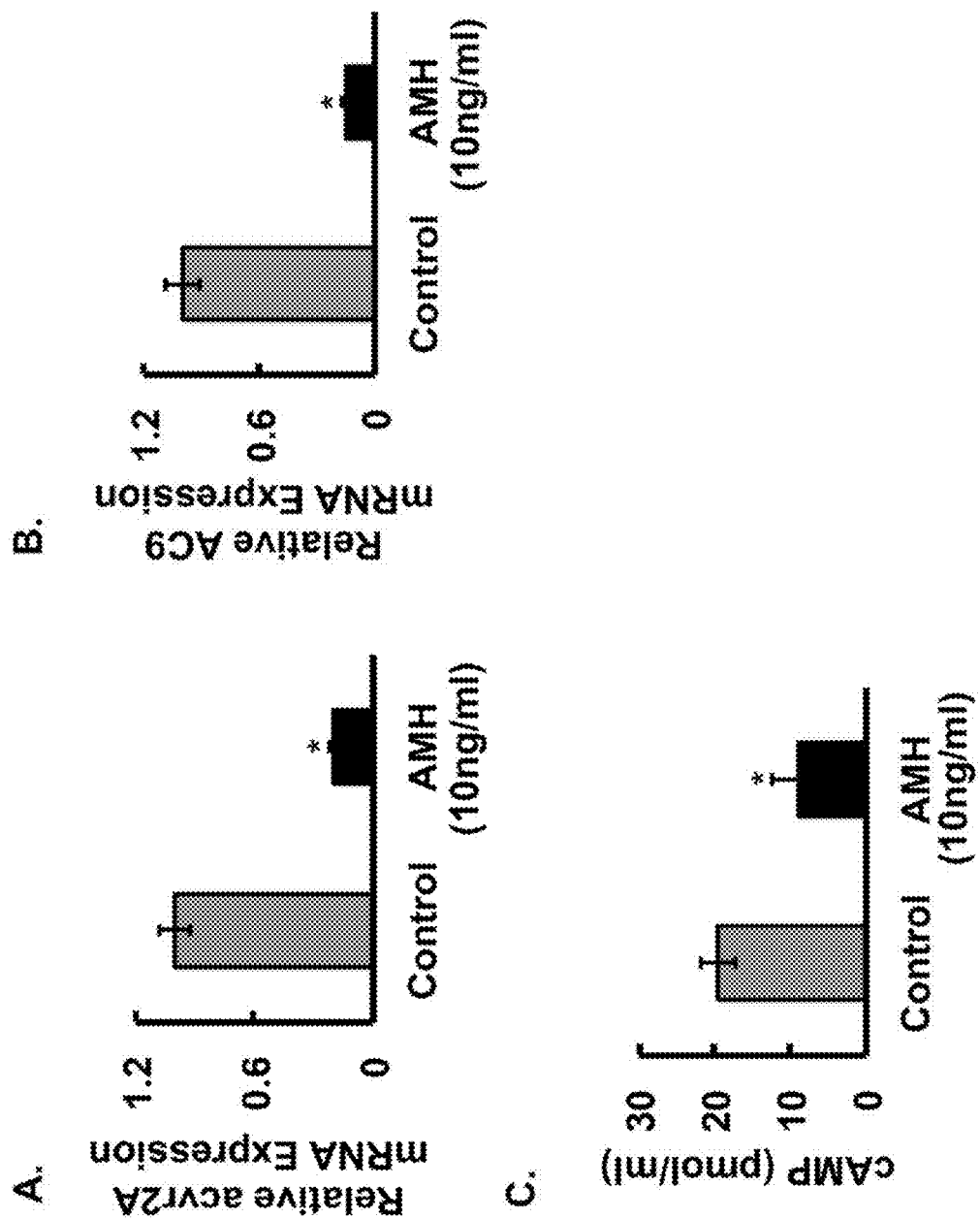
FIG. 17A through FIG. 17C, depicts the results of experiments where KGN cells cultured with DMEM:F-12 medium containing 10% (vol/vol) FBS and 1% penicillin and streptomycin. The cells were serum starved for 5 h, followed by 10 ng/ml of FSH stimulation in the presence or absence of 10 ng/ml of AMH for 18.

Total RNA was isolated by using mirVana miRNA Isolation Kit (Ambion/Life Technologies) and quantitative RT-PCR was performed using TaqMan MicroRNA reverse transcription kit and mouse miR-181a and miR-181b TaqMan MicroRNA Assays (Applied Biosystems) as described previously (Sen et al., 2014, PNAS 111:3008-13). GAPDH was used as an endogenous control and relative expression of miR-181a and miR-181b was calculated by using the ΔΔ Ct method miR-181 Inhibition In vitro down-regulation of miR181a b was performed as described previously (Sen et al., 2014, PNAS 111:3008-13). Briefly, primary mouse GCs were transfected with mouse hsa-miR-181a-3p or hsa-miR-181b-5p mirVana miR inhibitor or with nonspecific control (Ambion) for 48 h and then stimulated with AMH for 18 h. Specificity of knockdown was determined by measuring miR-181a and miR-181b expression levels (FIG. 17).

Western Blot Analysis

Western blots were performed as described previously (Ma et al., 2016, Endocrinology en20151750; Sen et al., 2014, PNAS 111:3008-13; Evaul and Hammes, 2008, J Biol Chem 283:27525-33). Primary antibodies used were Anti-Activin Receptor Type IIA antibody (EPR7407), Anti-ADCY9 antibody (ab110159) (Abcam) at 1:1000 and GAPDH at 1:5,000 (Cell Signaling Technology).

Superovulation and Follicle Count

Pre-pubertal and 8-9 week old mice were treated with AMH (300 ng) or vehicle for 4 weeks followed by 12 days of no treatment. Thereafter, these animals were subjected to superovulation regime as described previously (Ma et al., 2016, Endocrinology en20151750; Sen and Hammes, 2010, Mol Endocrinol 24:1393-403; Sen et al., 2014, PNAS 111: 3008-13). Briefly, mice (n=5 animals/treatment) were given a single IP injection of 5 U of pregnant mare serum gonadotropin (Sigma, St. Louis, Mo.) followed 48 h later by 5 U of human chorionic gonadotropin (Sigma). After an additional 18 h, oocyte/cumulus masses were surgically isolated from the oviduct and counted.

Statistical Analysis

Each in vitro experiment was repeated at least 3 times or more and data are displayed as mean±SEM. Statistical analysis was performed using Prism version 6 (GraphPad). ANOVA was used to detect differences between treatments. $P \leq 0.05$ was considered significant.

The results of the experiments are now described.

Figures 8A, 8B:
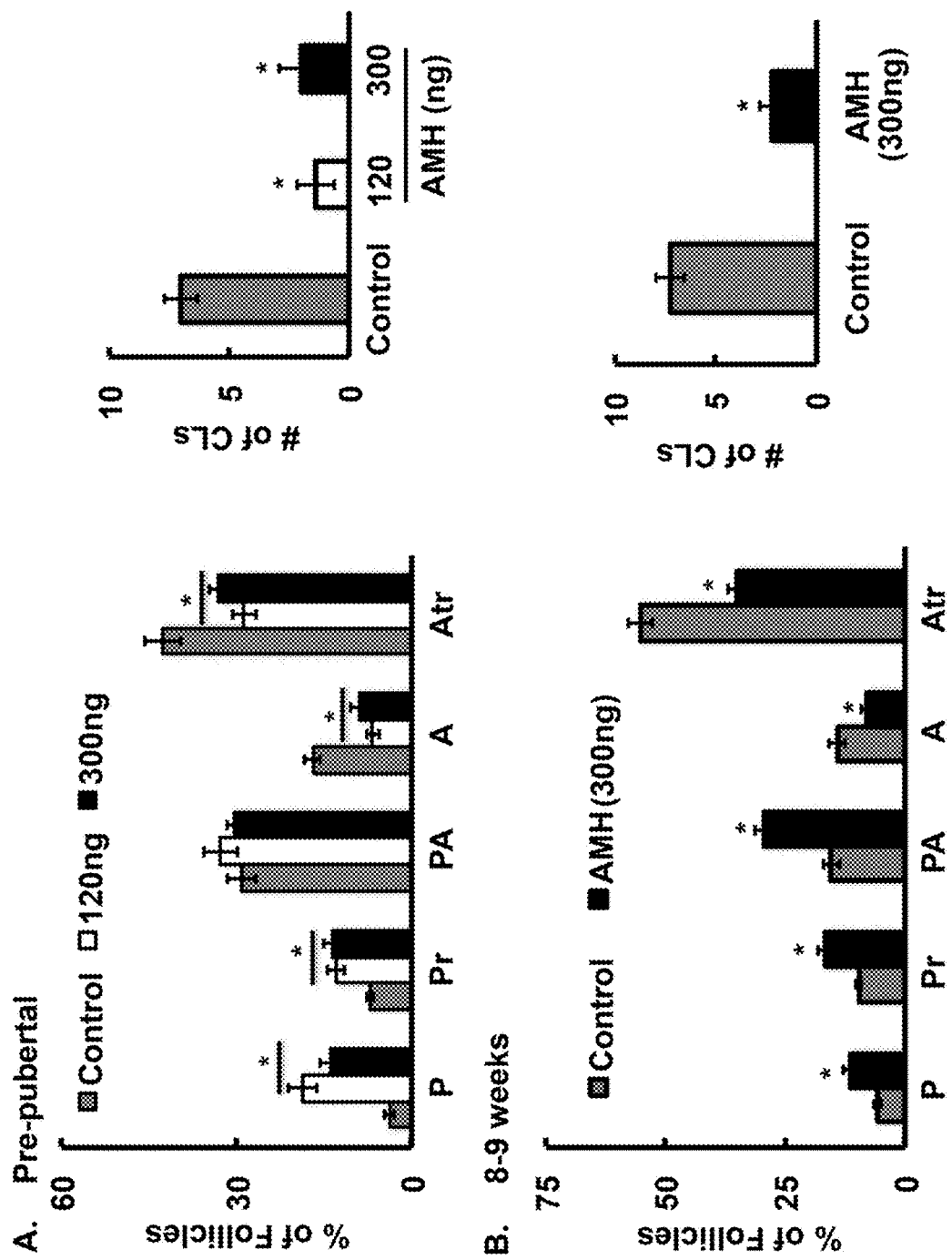
FIG. 8A and FIG. 8B, depicts the results of experiments demonstrating In vivo AMH treatment stalls/inhibits folliculogenesis and ovulation.

In Vivo AMH Treatment Stalls Follicular Development Through Inhibition of Ovarian Gene Expression and Steroidogenesis To determine the role of AMH in follicular development, ovarian morphology was studied in pre-pubertal (21 d old) and reproductive age (8-9 weeks old) mice treated with vehicle (control) or different concentrations (120 and 300 ng) of AMH for 4 weeks (n=5 animals/treatment group). Irrespective of concentration, the distribution of growing follicles was almost identical in pre-pubertal animals (FIG. 8A). AMH-treated pre-pubertal animals had significantly higher percentages of primordial, P (18.8±2.4% and 14±1.8% vs 3.9±0.9%) and primary, Pr (13.0±1.4% and 13.5±1.6% vs 7.2±0.6%) follicles relative to vehicle-treated animals, with significantly lower percentages of antral, A (6.7±1.1% and 9.1±1.6% vs 17.1±1.5%), and atretic, Atr (28.7±2.0% and 33.0±1.7% vs 42.7±3.1%) follicles. In addition, these animals had fewer of corpora lutea, CL (1.4±0.8 and 2±0.9 vs 7±0.7) relative to control animals (FIG. 8B). AMH treatment of 8-9 week old mice resulted in a similar pattern of ovarian morphology. While percentages of primordial (11.5±1.2% vs 5.7±0.9%) primary (16.4±1.7% vs 9.6±0.6%) and pre-antral (29.3±1.8% vs 15.3±1.8%) follicles were significantly higher, antral (7.9±1.1% vs 14.1±1.7%) and atretic (34.9±1.9% vs 55.2±2.5%) follicle percentages as well as the number of corpora lutea (2.2±0.6 vs 7.2±0.7) were significantly lower in AMH versus control treated animals (FIGS. 8B and 8C). These results suggest, that while AMH in general has a stalling or inhibiting effect on follicular development, preventing follicles from reaching the antral stage and being ovulated to produce corpora lutea, it also has anti-apoptotic properties.

Figures 9A, 9B, 9C:
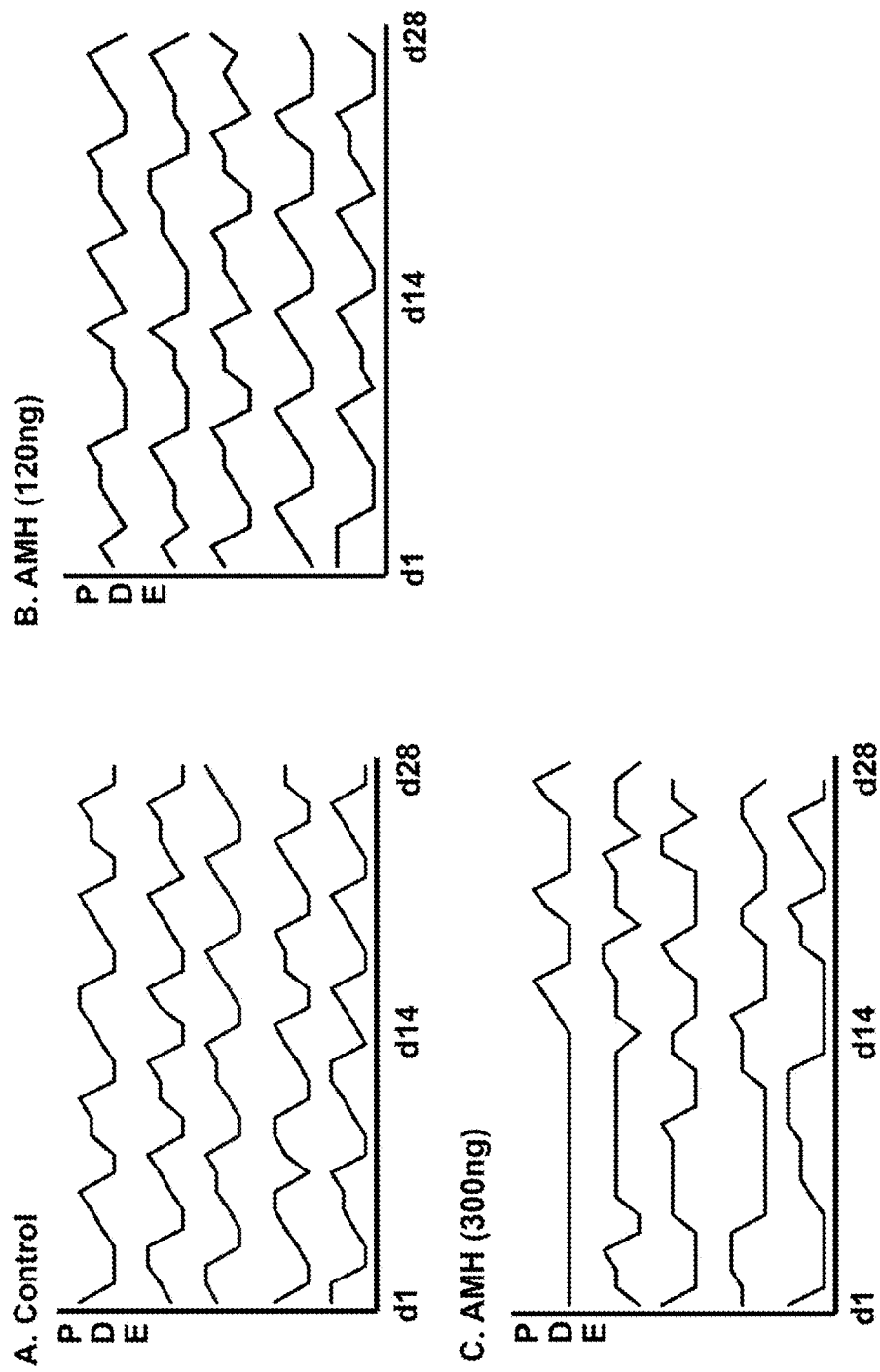
FIG. 9A through FIG. 9C, depicts the results of experiments demonstrating in vivo AMH treatment disrupts estrous cycling in reproductive age mice.

To determine whether abnormal estrous cycling in part caused the negative effect of AMH on follicular development, vaginal smears from 8-9 week old mice treated with vehicle (control) or different concentrations (120 and 300 ng) of AMH for 4 weeks (n=5 animals/treatment) were examined over the course of one month (FIG. 9). While animals treated with vehicle (FIG. 9A) or 120 ng of AMH (FIG. 9B) cycled normally, 300 ng AMH treatment disrupted the estrous cyclicity (FIG. 9C).

Figures 10A, 10B:
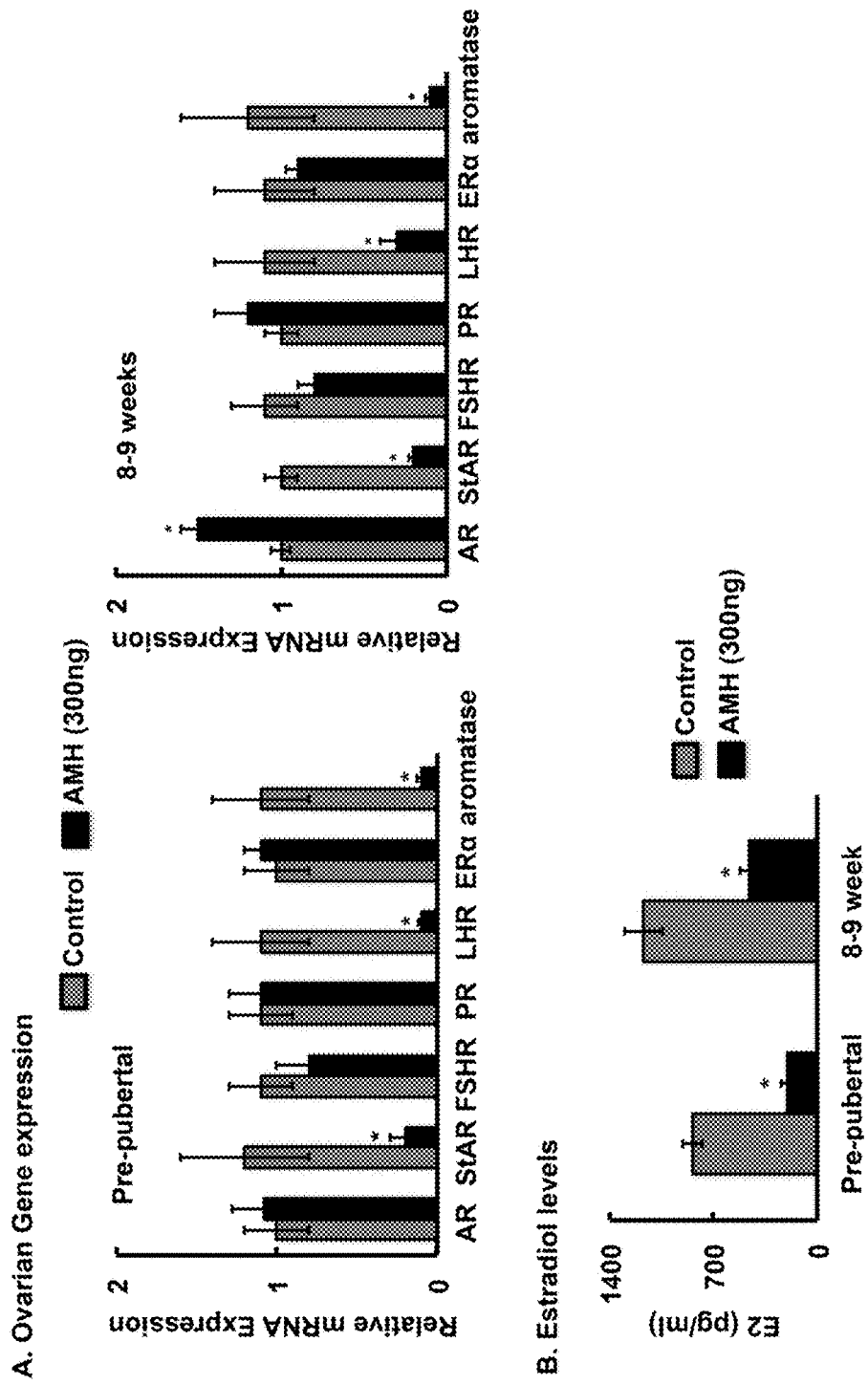
FIG. 10A and FIG. 10B, depicts the results of experiments demonstrating in vivo AMH treatment decreases ovarian gene expression and serum estradiol levels. Pre-pubertal and reproductive age 8-9 week old mice (n=5 ovaries from five different mice/age group) were subjected to daily IP injection of vehicle or AMH (300 ng) for 4 weeks.

To gain further insight into the effects of AMH on follicular development, ovarian gene expression pattern was determined in ovaries isolated from pre-pubertal (21 d old) and reproductive aged (8-9 week old) mice treated with vehicle (control) or AMH (300 ng) for 4 weeks (n=5 animals/treatment). Results show (FIG. 10A) that, irrespective of age, AMH treatment significantly decreased the expression of steroidogenic acute regulatory protein (StAR), luteinizing hormone receptor (LHR) and Cyp19a1 (aromatase) mRNA levels compared to vehicle treated controls. There was also a trend towards lower follicle stimulating hormone receptor (FSHR) levels, especially in ovaries of 8-9 week old animals treated with AMH. Additionally, ovaries isolated from AMH treated 8-9 week old animals had significantly higher levels of androgen receptor (AR) expression.

Since StAR and aromatase are critical for steroidogenesis, serum estradiol levels (FIG. 10B) were further measured in these animals. As expected, estradiol levels were significantly lower in AMH-treated pre-pubertal and 8-9 week old animals relative to controls. These results suggest that the inhibitory or stalling effects of AMH on follicular development are likely mediated through inhibition of ovarian gene expression important for steroidogenesis (StAR and aromatase) and ovulation (LHR).

AMH Inhibits FSH Effects of Follicular Development

Figures 11A, 11B, 11C:
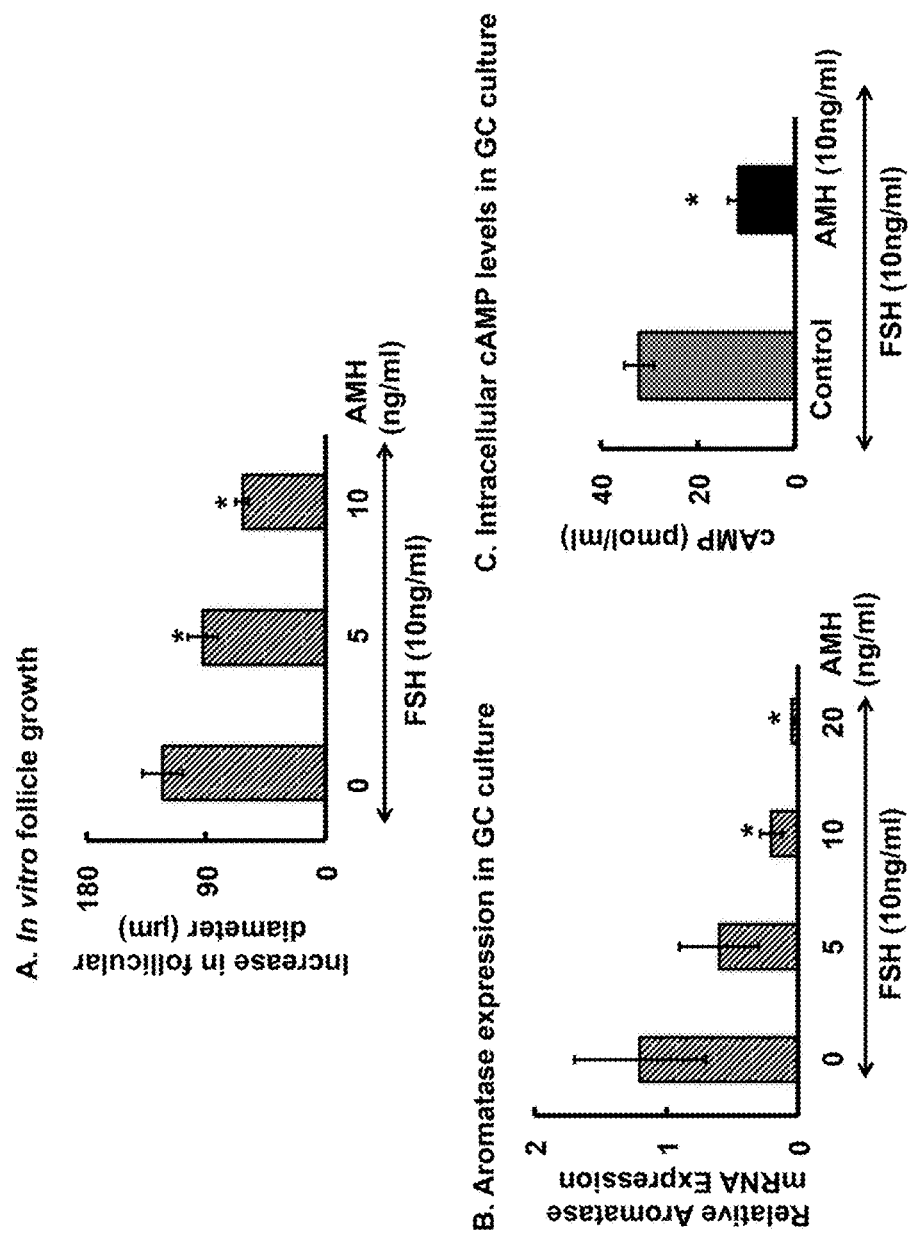
FIG. 11A through FIG. 11C, depicts the results of experiments demonstrating in vitro AMH treatment inhibits FSH-stimulated follicular growth, aromatase expression and intracellular cAMP levels.

To further demonstrate AMH effects on follicular growth, pre-antral follicles were mechanically isolated from ovaries of 21 d old female mice and cultured them in vitro for 4 days in the presence of FSH with/without AMH (5 and 10 ng/ml) (FIG. 11A). Follicular growth was determined as a measure of increase in follicular diameter of individual follicles from the beginning to the end of culture. FIG. 4A shows the average increase in diameter (10 follicles/treatment) isolated from 5 separate animals: AMH treatment in a concentration dependent manner significantly inhibited FSH-induced in vitro follicle growth. Since it is well-established that FSH induces intra-cellular cAMP levels and aromatase gene expression in GCs, AMH effects on these FSH actions were directly determined in vitro. In mouse primary GC culture, AMH treatment significantly decreased FSH-induced aromatase mRNA expression (FIG. 11B) in a dose dependent manner, and also inhibited FSH-stimulated intra-cellular cAMP levels (FIG. 11C).

Figures 12A, 12B:
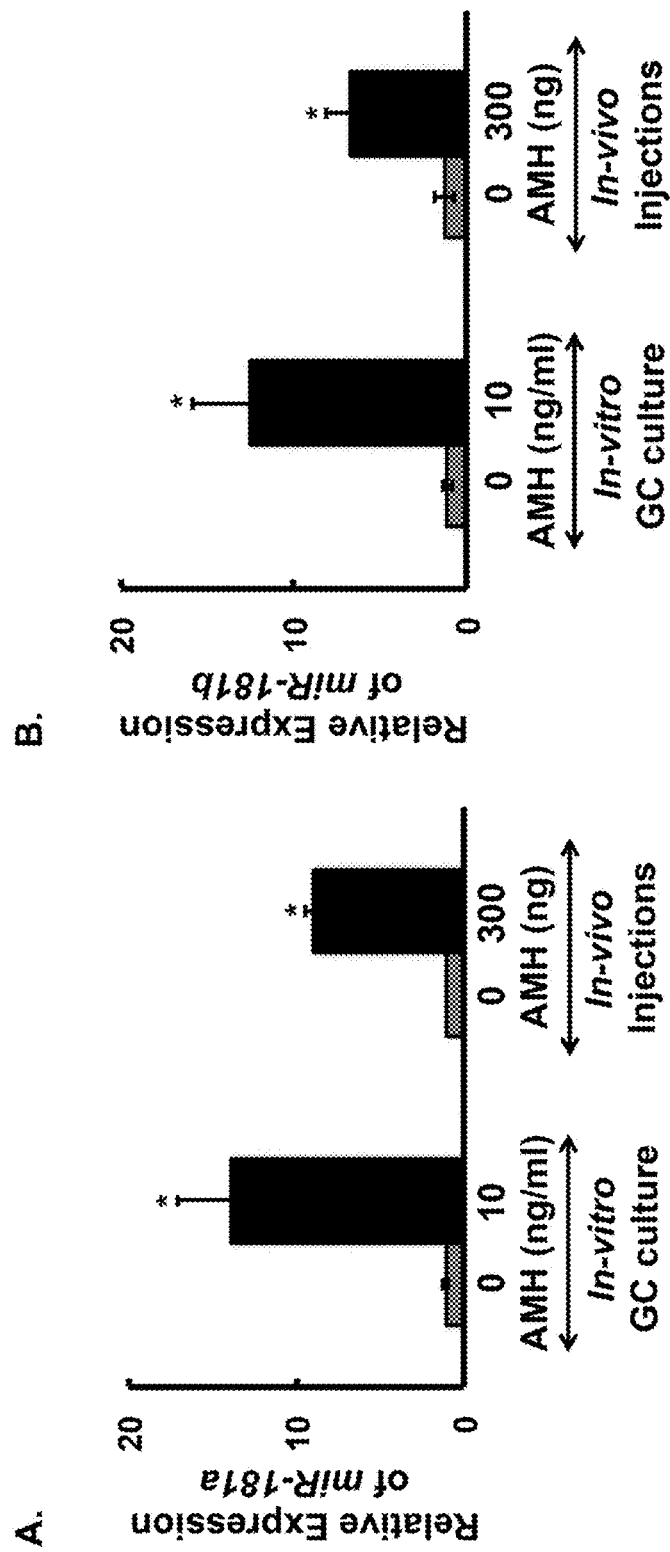
FIG. 12A and FIG. 12B, depicts the results of experiments demonstrating AMH treatment induces miR-181a and miR-181b expression both in vivo and in vitro.

Inhibitory Effects of AMH on Follicular Development are Mediated Through Induction of miR-181a and 181b in GCs In this study it is reported that AMH regulates follicular development by inducing the expression of miR-181a and miR-181b. AMH treatment in vitro (primary GC cultures) and in vivo (in ovaries of mice injected with AMH for 4 weeks), significantly induced the expression of miR-181a (FIG. 12A) and miR-181b (FIG. 12B). Interestingly, previous studies in GCs (Zhang et al., 2013, PLoS One 8:e59667) and cervical cancer cells (Yang et al., 2014, FEBS Lett 588:124-30) show that miR-181a and miR-181b targets activin receptor 2A (acvr2A) and adenylate cyclase 9 (ADCY9), respectively.

Figures 13A, 13B:
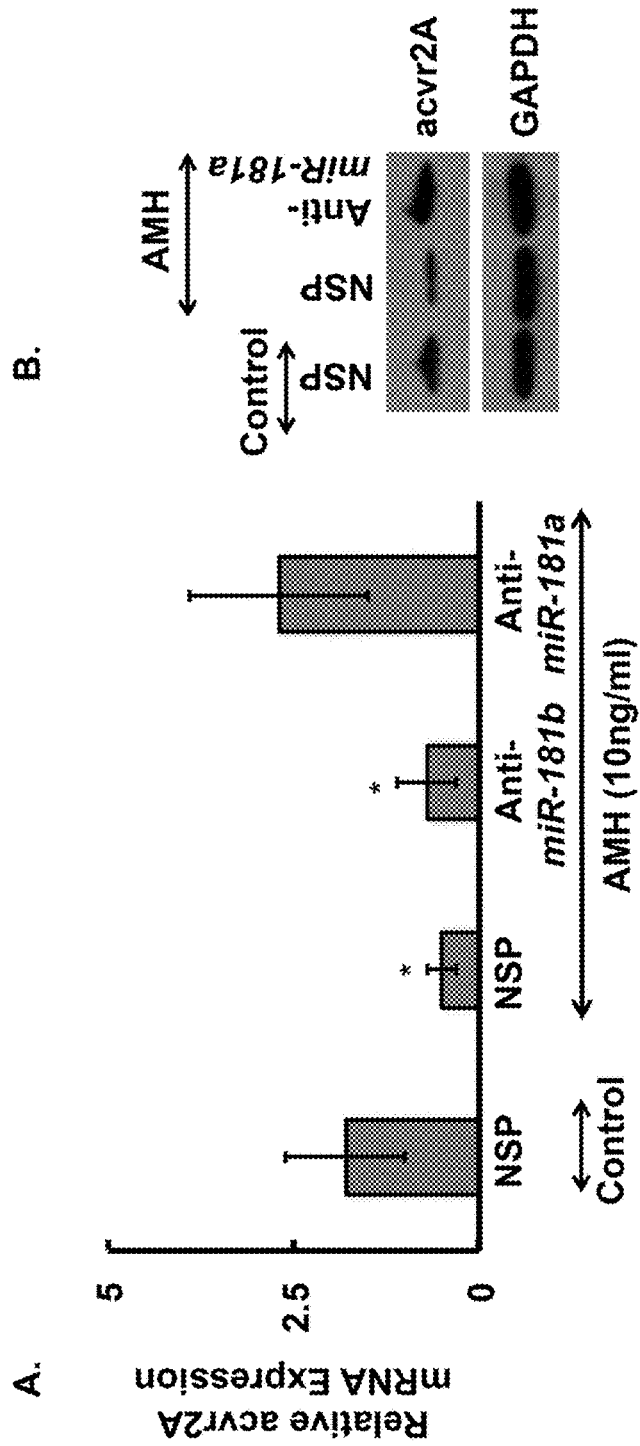
FIG. 13A and FIG. 13B, depicts the results of experiments demonstrating AMH-induced miR-181a targets activin receptor 2A (acvr2A). Primary mouse GCs isolated from 8-9 week old mice were transfected with mouse hsa-miR-181a-3p or hsa-miR-181b-5p mirVana miR inhibitor or with nonspecific control (NSP) for 48 h and then stimulated with/without AMH (10 ng/ml) for 18 h.

Using TargetScan algorithm 6.2 (Whitehead Institute for Biomedical Research), it was also found that acvr2A and ADCY9 are potential targets of miR-181a and miR-181b, respectively. Therefore, whether AMH treatment inhibits acvr2A (FIG. 13A) and ADCY9 (FIG. 14A) expression was tested.

AMH, in fact, significantly decreased acvr2A and ADCY9 mRNA (FIGS. 13A and 14A, respectively) and protein levels (FIGS. 13B and 14B, respectively) in mouse primary GC cultures. Moreover, down regulation of miR-181a and miR-181b (FIG. 17) in primary GCs using miR-181a and miR-181b inhibitor, significantly rescued these inhibitory effects of AMH on acvr2A (FIG. 13) and ADCY9 levels (FIG. 14), respectively. Notably, anti-miR-181a and anti-miR-181b did not have any effect on ADCY9 and acvr2A levels, respectively, thereby demonstrating the specificity of these miRNAs to their targets.

Figures 14A, 14B, 14C:
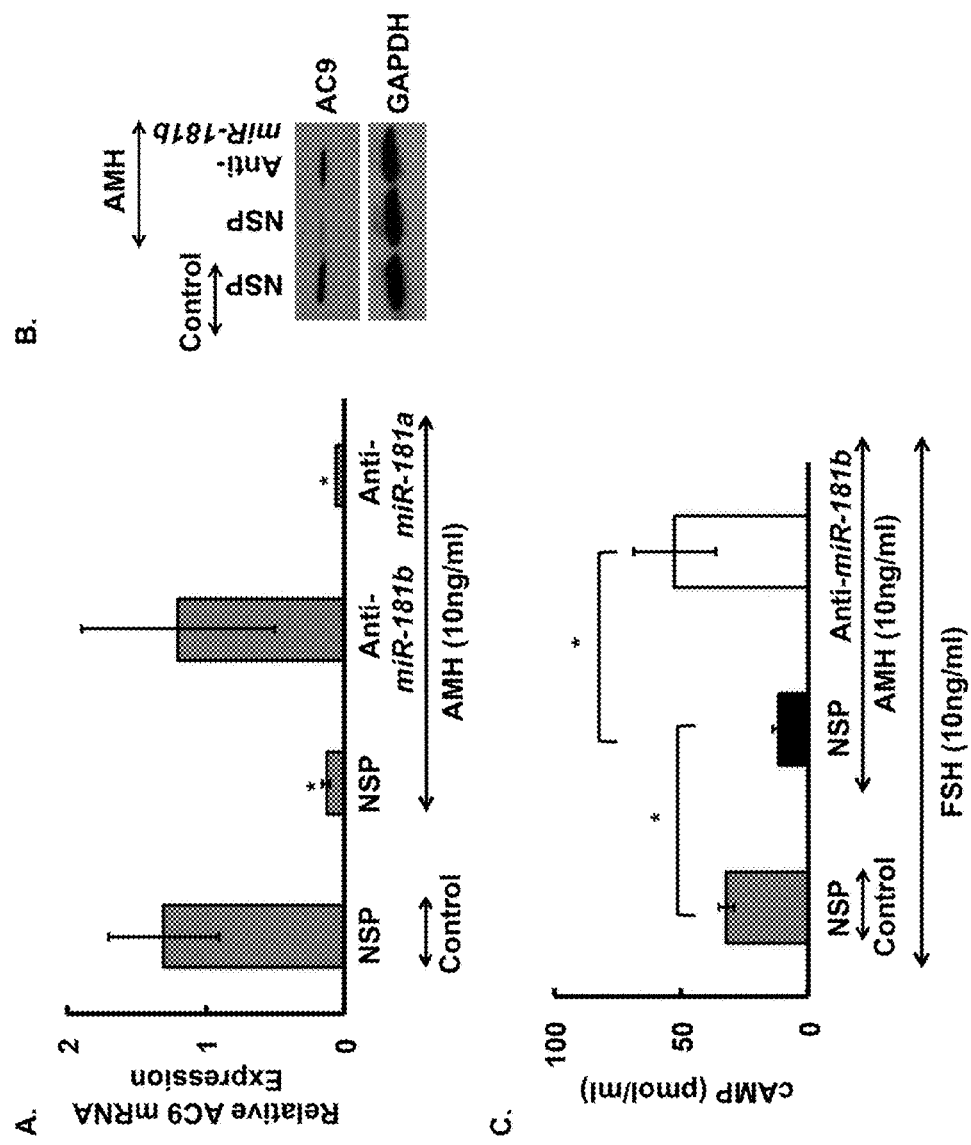
FIG. 14A through FIG. 14C, depicts the results of experiments demonstrating negative effects of AMH on FSH-stimulated cAMP levels are mediated through decline in adenylate cyclase 9 (ADCY9) levels targeted by AMH-induced miR-181b. Primary mouse GCs isolated from 8-9 week old mice were transfected with mouse hsa-miR-181a-3p (anti-miR-181a) or hsa-miR-181b-5p (anti-miR-181b) mirVana miR inhibitor or with nonspecific control (NSP) for 48 h and then stimulated with/without AMH (10 ng/ml) for 18 h.

To further determine if the inhibitory effects of AMH on FSH-stimulated cAMP levels are mediated through induction of miR-181b and via targeting ADCY9, FSH-stimulated intra-cellular cAMP levels were measured in non-specific and anti-miR-181b inhibitor treated primary GC cultures in presence/absence of AMH. FIG. 14C demonstrates that down-regulation of miR-181b significantly rescued AMH-induced decrease in FSH-stimulated intra-cellular cAMP levels.

Figure 18:
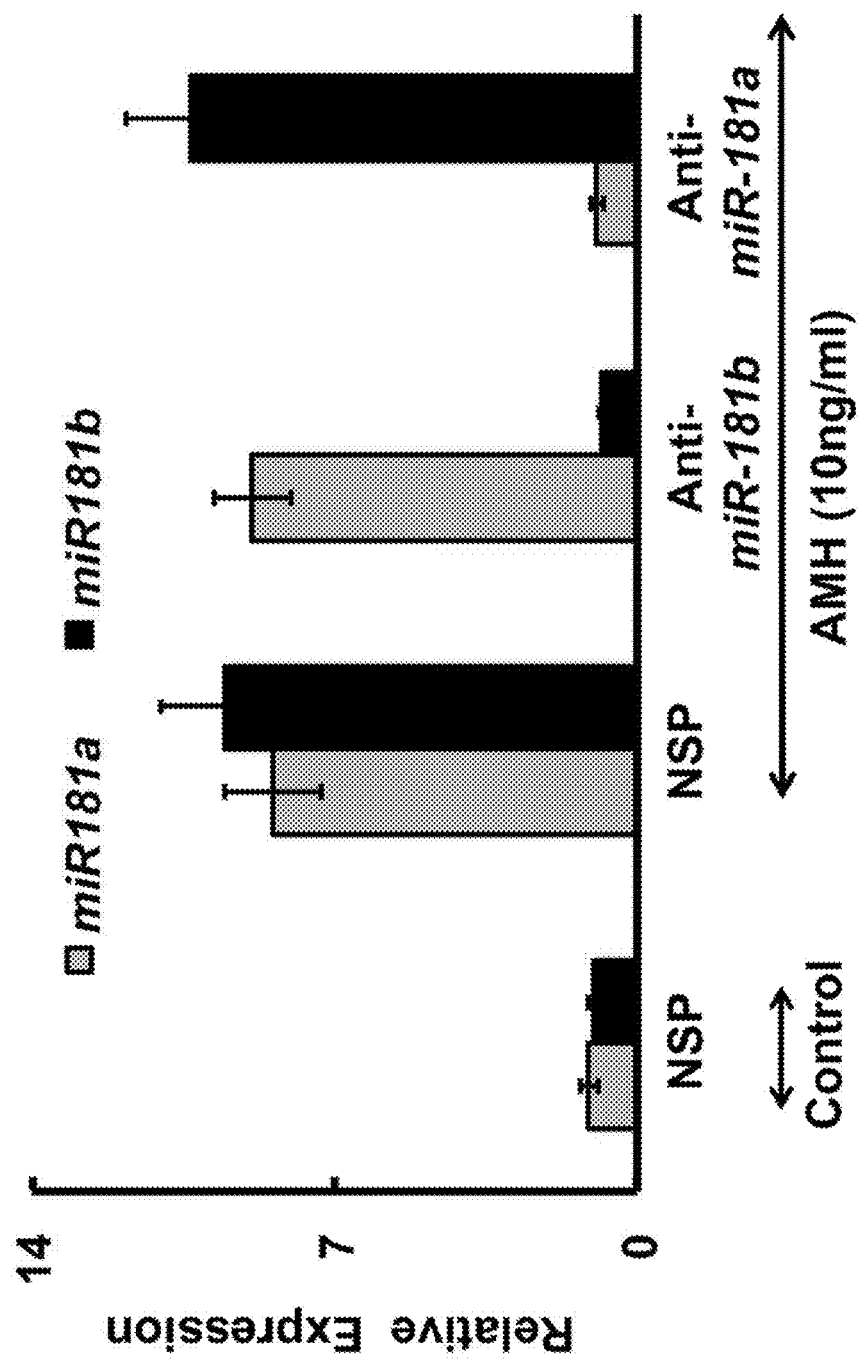
FIG. 18 depicts the relative expression of miR-181a and miR-181b in primary mouse GC cultures transfected with mouse has-miR-181a-3p (Anti-miR-181a) or has-miR-181b-5p (Anti-miR-181b) mirVana miR inhibitor or with non-specific control (NSP) and treated with/without AMH.

Lastly, the observations were extended from mouse GCs to a well-established human GC cancer cell line, KGN cells. FIG. 18 demonstrates that, similar to mouse GCs, AMH treatment also decreased acvr2A and ADCY9 mRNA as well as intra-cellular cAMP levels in KGN cells, thereby suggesting that the underlying mechanisms of AMH actions are likely conserved across species.

AMH Priming Enhances Oocyte Ovulation

Figures 15A, 15B:
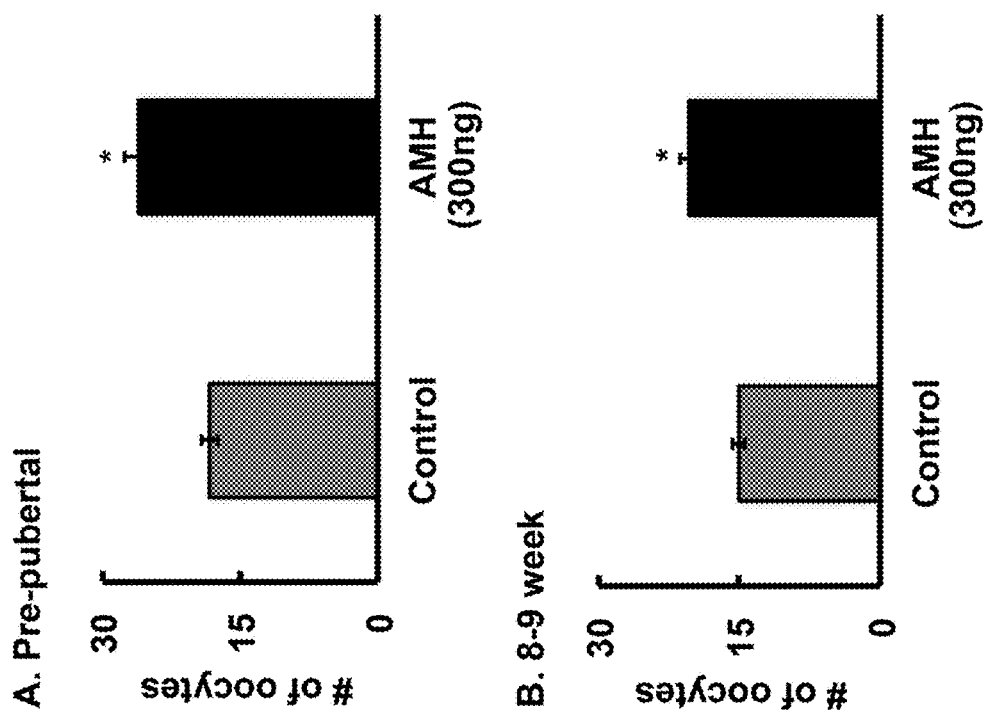
FIG. 15A and FIG. 15B, depicts the results of experiments demonstrating AMH pre-treatment prior to superovulation regime enhances oocyte yield.

Finally, given that AMH blocks follicular development resulting in overall follicle accumulation, it was examined whether AMH priming followed by superovulation would increase the number of ovulated oocytes. Pre-pubertal and 8-9 week old mice were treated with AMH (300 ng) or vehicle for 4 weeks followed by 12 days of no treatment. Thereafter, these animals were subjected to superovulation regime and ovulated oocytes were then isolated from the oviducts of the animals and counted. Results (FIG. 15) show that, irrespective of age, AMH-treated animals superovulated more oocytes compared to vehicle treated mice (pre-pubertal: 26±1.5 vs 18.3±0.9 and 8-9 week old: 20.3±0.9 vs 15±0.6).

AMH Inhibitory Effect on Folliculogenesis is Mediated Through miR-181a and 181b Induction To date, most of studies investigating AMH actions in the ovary have been limited to AMHKO mouse model or in vitro studies. These data show direct in vivo effects of AMH administration on follicular development, and provide possible mechanistic insights into AMH actions during follicular development. First, it was shown that AMH treatment in vivo negatively affects expression of a large number of genes involved in folliculogenesis, lowers serum estradiol levels and, notably, has a stalling or inhibitory effect on follicular development. Second, similarly to previous studies (Durlinger et al., 2001, Endocrinology 142:4891-9; Chang et al., 2013, Fertil Steril 100:585-92 e581; Pellatt et al., 2011, Fertil Steril 96:1246-51), direct inhibitory effects of AMH on FSH-induced follicular growth, aromatase expression and intra-cellular cAMP levels were demonstrate in vitro. More importantly, it is reported herein that AMH induces the expression of two microRNAs; (i) miR-181a and (ii) miR-181b in GCs. These AMH-induced miRNAs in turn target acvr2A and ADCY9, respectively, which likely mediate the negative effects of AMH on follicular development. Finally, exogenous AMH treatment enhances gonadotropin-induced ovulation in mice.

While previous studies in AMHKO mouse model (Durlinger et al., 1999, 140:5789-96) reported that loss of AMH results in accelerated folliculogenesis leading to POI, these studies show that exogenous recombinant AMH administration inhibits folliculogenesis, causing follicles to stall at different stages of development. Both of these two studies, therefore, establish AMH as a critical regulator of follicular development. Intriguingly, it was also found that AMH treatment significantly lowers the percentage of atretic follicles, thereby providing for the first time experimental evidence for the long suspected notion (Seifer and Merhi, 2014, J Assist Reprod Genet 31:1403-7) that AMH may have anti-atretic properties. What mediates the anti-atretic properties of AMH is not known and needs further studies.

These data also show that AMH treatment negatively affects estrous cycling in reproductive age animals and prevents ovulation. This effect may be due to decreased LHR mRNA levels observed in AMH-treated animals. AMH receptors are, however, not only expressed in the ovary but also in the pituitary (Bedecarrats et al., 2003, PNAS 100: 9348-53). Neuroendocrine effects of AMH on folliculogenesis and ovulation rate can, therefore, not be discounted. Interestingly, AMH and AMHRII (AMH receptor II) are overexpressed in oligo/anovulatory but not in normal-ovulatory PCOS women. A potential role of the AMH/AMHR-II system in the follicular arrest observed in PCOS has been suggested previously (Pierre et al., 2013, Hum Reprod 28:762-9).

This study also demonstrates the genes affected by AMH treatment in vivo. Surprisingly, in reproductive age mice (8-9 week old), AMH treatment induced androgen receptor (AR) mRNA levels. Androgen receptors are mainly expressed in small growing follicles (Prizant et al., 2014, J Endocrinol 222:R141-51). AMH-induced increase in AR mRNA levels may, therefore, be consequence of increased numbers of small follicles that are stalled due to AMH treatment. Whether AMH indeed directly affects AR expression needs further elucidation. More importantly, aromatase, StAR and LHR mRNA levels, inhibited by in vivo AMH treatment, are all downstream targets of FSH signaling. Though not reaching significance, interestingly in pre-pubertal as well as reproductive aged animals a trend toward AMH-induced decrease of FSH receptor (FSHR) mRNA levels was found. Similar results have also been reported in vitro, in human luteinizing GCs (Pellatt et al., 2011, Fertil Steril 96:1246-51; Prapa et al., 2015, J Assist Reprod Genet 32:1079-88; Grossman et al., 2008, Fertil Steril 82:1364-70). It is now well accepted that AMH decreases the responsiveness of growing follicles to FSH and inhibits the recruitment of primordial follicles into the pool of growing follicles. Furthermore, these AMH effects are suggested primarily to be mediated by inhibiting FSH-induced cAMP levels, aromatase (cyp19a) expression and estradiol levels as well as by blocking FSH-stimulated follicular growth (Visser et al., 2012, Nat Rev Endocrinol 8:331-41; La Marca et al., 2009, Hum Rprod 24:2264-75). But how exactly AMH inhibits FSH actions is so far not known. That AMH, through miR-181a and miR-181b, negatively regulates acvr2A and ADCY9, likely, offers a mechanistic explanation.

AMH is a member of the transforming growth factor-β (TGF-β) superfamily and previous studies in ovarian (Parikh et al., 2014, Nat Commun 5:2977) and breast cancer (Taylor et al., 2013, J Clin Invest 123:150-63), osteoblastic differentiation (Bhushan et al., 2013, Int J Biochem Cell Biol 45:696-705) and in hepatic cells (Wang et al., 2010, Oncogene 29:1787-97) that TGF-β signaling regulates miR-181a and miR-181b expression. Interestingly, in mouse GCs, miR-181a targets the activin receptor (acvr2a) (Zhang et al., 2013, PLoS One 8:e59667). It is well-established that activin, also a member of the TGF-β superfamily, is an important regulator of follicular development, and promotes growth of preantral follicles and proliferation of GCs (Cossingy et al., 2012, Reproduction 143:221-9). Similarly, ADCY9 is a very well established target for miR-181b (Yang et al., 2014, FEBS Lett 588:124-30; Zhuang et al., 2014, Cell Death Dis 5:e1161) and is involved in the synthesis of cAMP from ATP. There are about nine membrane-associated members of mammalian adenylate cyclase (AC1-9) isoforms that have been identified so far. ADCY9 is expressed in various organs including the ovary (Ludwig and Seuwen, 2002, J Recept Signal Transduct Res 22:79-

110) and is insensitive to forskolin (Hacker et al., 1998, 50:97-104; Cumbay et al., 2004, J Pharmacol Exp Ther 310:108-15).

Figure 16:
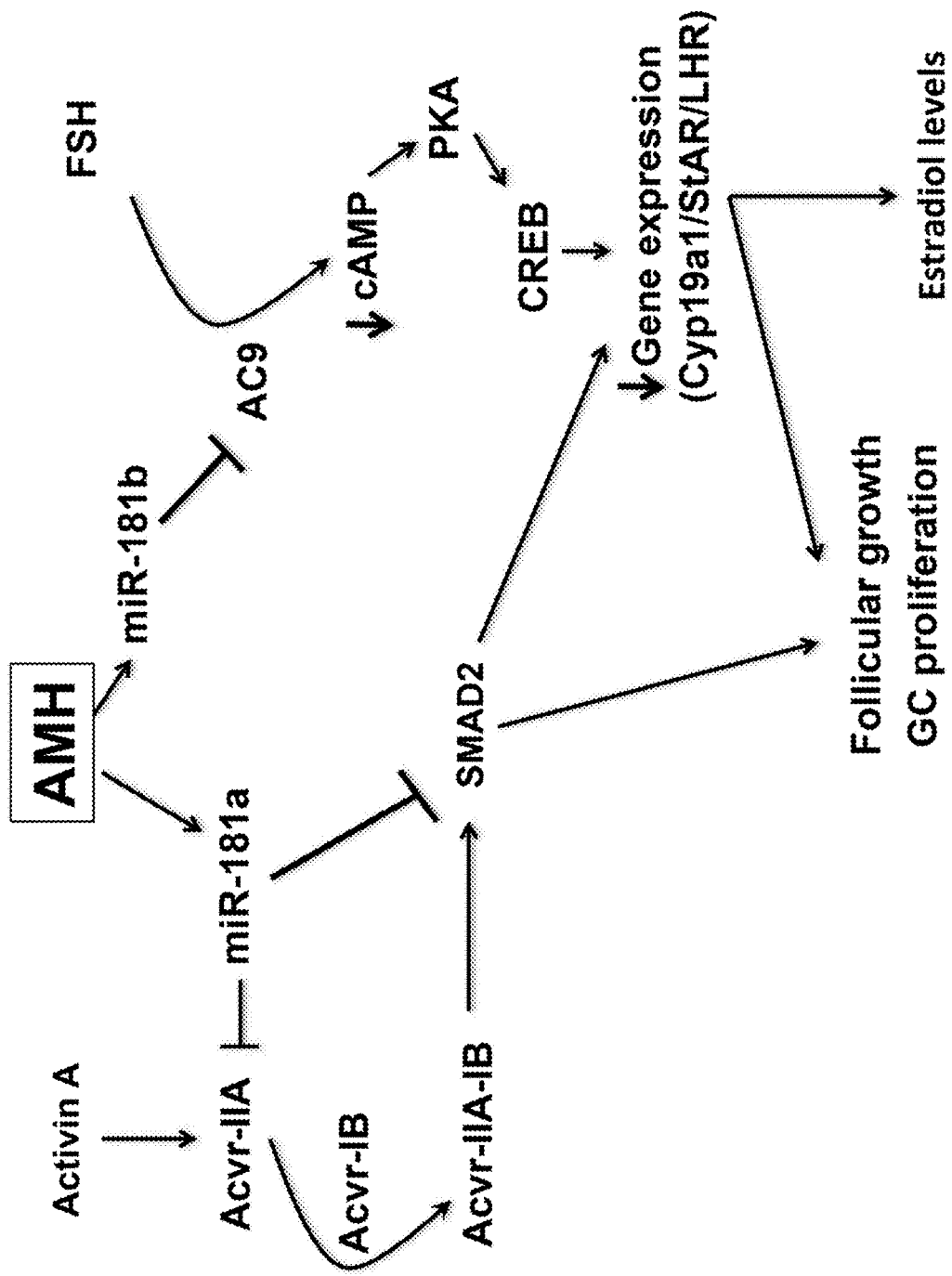
FIG. 16 depicts the proposed model of intracellular mechanism(s) of AMH actions in granulosa cells. AMH through induction of miR-181a targets activin receptor 2A (acvr2A) leading to disruption of activin effects on folliculogenesis like follicular growth, GC proliferation and gene expression. AMH also induces miR-181b expression that targets adenylate cyclase 9 (ADCY9), thereby decreasing FSH-induced cAMP levels and resulting in reduction in FSH sensitivity and/or suppression of FSH signaling. This leads to inhibition of downstream genes like aromatase, StAR and LHR, all of which are FSH regulated. All of these effects ultimately lead to lower estradiol levels and inhibition/stalling of folliculogenesis.

Therefore, in summary the following model is proposed (FIG. 16): AMH, through induction of miR-181a expression, targets acvr2a leading to disruption of activin effects on follicular growth. Furthermore, AMH induces miR-181b expression that targets ADCY9, thereby decreasing cAMP levels and resulting in reduction of FSH sensitivity and/or suppression of FSH signaling. This leads to inhibition of downstream genes like aromatase, StAR and LHR, all of which are FSH-regulated. In fact, aromatase gene expression is also regulated by activin signaling through the acvr-Smad2 pathway (Nomura et al., 2013, Biochem Biophys Res Commun 436:443-8) and, thus, can also be negatively regulated by AMH-induced miR-181a expression. All of these effects ultimately lead to lower estradiol levels and inhibition/stalling of folliculogenesis.

Currently, in women AMH is exclusively used as a diagnostic and/or prognostic marker. Absence of mechanistic insights into AMH actions in the ovary has been a significant limitation in using AMH as a therapeutic agent. Since AMH appeared to be a powerful brake on follicular transition, as a proof of concept, it was sought to determine whether pre-treatment with exogenous recombinant AMH of mice, subjected to superovulation, increases oocyte yields. The hypothesis was that it might be possible through AMH administration to retrieve more oocytes by creating a pool of stalled non-atretic small follicles, which then is released by stopping AMH treatment, followed by superovulation. Though, indeed, a statistically significant increase in oocyte yield following AMH pre-treatment is demonstrated herein, this increase was not as large as expected. There are various possible explanations for this finding: For example, the effect of AMH may be subdued in polyovulatory species like mice. The experiment demonstrated, however, that AMH can, indeed, be a potential therapeutic option for women with low functional ovarian reserve, whether due to age or premature ovarian aging.

AMH has a stalling/inhibitory effect on folliculogenesis and ovulation that is mediated at least in part through the induction of two miRs, miR-181a and miR-181b, which target acvr2 an ADCY9, leading to a decline in FSH signaling/sensitivity, ovarian gene expression and follicular growth. Moreover, accumulation of follicles due to the stalling effect of AMH may be used as a potential therapeutic option.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating infertility in a subject comprising administering to the subject an effective amount of a composition comprising anti-Mullerian hormone (AMH), wherein the AMH comprises the amino acid sequence set forth in SEQ ID NO:1; and wherein the AMH is administered at a dose in the range of about 22,000 ng/day to about 44,000 ng/day for a period of time from about 30 days to about 90 days.

2. The method of claim 1, wherein infertility in the subject is characterized by at least one selected from the group consisting of diminished ovarian reserve (DOR), natural aging, premature ovarian aging, and gonadotoxic treatment.

3. The method of claim 1, wherein the subject is human.

4. A method of increasing the number of collected oocytes during superovulation in a subject, the method comprising:
   a) administering to the subject an effective amount of AMH each day for a first period of time;
   b) inducing superovulation in the subject after a second period of time where no AMH is delivered to the subject, wherein the AMH comprises the amino acid sequence set forth in SEQ ID NO: 1.

5. The method of claim 4, wherein superovulation is induced by administering to the subject at least one selected from the group consisting of a gonadotropin, follicle stimulating hormone (FSH), luteinizing hormone (LH), clomiphene, a selective estrogen-receptor modulator (SERM), and a aromatase inhibitor.

6. The method of claim 4, wherein the first period of time is in the range of about 1 day to about 90 days.

7. The method of claim 6, wherein AMR is administered at a dose in the range of about 22,000 ng/day to about 44,000 ng/day, for a first duration of about 90 days.

8. The method of claim 4, wherein the second period of time is in the range of about 0 days to about 30 days.

* * * * *

SEQUENCE LISTING

```
<160> NUMBER OF SEQ ID NOS: 1

<210> SEQ ID NO 1
<211> LENGTH: 560
<212> TYPE: PRT
<213> ORGANISM: Homo sapiens

<400> SEQUENCE: 1

Met Arg Asp Leu Pro Leu Thr Ser Leu Ala Leu Val Leu Ser Ala Leu
1               5                  10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
    130                 135                 140

Ser Leu Arg Phe Gln Glu Pro Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175
```

```
Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

Gly Ser Gly Leu Ala Leu Thr Leu Gln Pro Arg Gly Glu Asp Ser Arg
    210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Pro Arg Ser Glu
                245                 250                 255

Pro Ala Pro Leu Pro Ala His Gly Gln Leu Asp Thr Val Pro Phe Pro
            260                 265                 270

Pro Pro Arg Pro Ser Ala Glu Leu Glu Glu Ser Pro Pro Ser Ala Asp
        275                 280                 285

Pro Phe Leu Glu Thr Leu Thr Arg Leu Val Arg Ala Leu Arg Val Pro
    290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
                325                 330                 335

Glu Arg Leu Leu Asp Gly Glu Glu Pro Leu Leu Leu Leu Leu Arg Pro
            340                 345                 350

Thr Ala Ala Thr Thr Gly Asp Pro Ala Pro Leu His Asp Pro Thr Ser
        355                 360                 365

Ala Pro Trp Ala Thr Ala Leu Ala Arg Arg Val Ala Ala Glu Leu Gln
    370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Leu Ala Leu Cys Pro Gly Gly Pro Gly
                405                 410                 415

Gly Leu Gly Asp Pro Leu Arg Ala Leu Leu Leu Leu Lys Ala Leu Gln
            420                 425                 430

Gly Leu Arg Val Glu Trp Arg Gly Arg Asp Pro Arg Gly Pro Gly Arg
        435                 440                 445

Ala Gln Arg Ser Ala Gly Ala Thr Ala Ala Asp Gly Pro Cys Ala Leu
    450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
                485                 490                 495

Ser Asp Arg Asn Pro Arg Tyr Gly Asn His Val Val Leu Leu Leu Lys
            500                 505                 510

Met Gln Val Arg Gly Ala Ala Leu Ala Arg Pro Pro Cys Cys Val Pro
        515                 520                 525

Thr Ala Tyr Ala Gly Lys Leu Leu Ile Ser Leu Ser Glu Glu Arg Ile
    530                 535                 540

Ser Ala His His Val Pro Asn Met Val Ala Thr Glu Cys Gly Cys Arg
545                 550                 555                 560
```